United States Patent
Tornoe et al.

(10) Patent No.: US 8,299,071 B2
(45) Date of Patent: *Oct. 30, 2012

(54) SUBSTITUTED PYRIDINE DERIVATIVES

(75) Inventors: Christian Wenzel Tornoe, Kgs. Lyngby (DK); Nikolay Khanzhin, Humlebaek (DK); Mario Rottlander, Greve (DK); William Patrick Watson, Vanløse (DK); Daniel Rodriguez Greve, Stenlose (DK)

(73) Assignee: H. Lundbeck A/S, Valby (DK)

( * ) Notice: Subject to any disclaimer, the term of this patent is extended or adjusted under 35 U.S.C. 154(b) by 36 days.

This patent is subject to a terminal disclaimer.

(21) Appl. No.: 12/881,263

(22) Filed: Sep. 14, 2010

(65) Prior Publication Data

US 2011/0003811 A1 Jan. 6, 2011

Related U.S. Application Data

(63) Continuation of application No. 11/817,340, filed as application No. PCT/DK2006/000123 on Mar. 2, 2006, now Pat. No. 7,812,020.

(60) Provisional application No. 60/658,428, filed on Mar. 3, 2005.

(30) Foreign Application Priority Data

Mar. 3, 2005 (DK) ................................. 2005 00321

(51) Int. Cl.
*C07D 413/04* (2006.01)
*C07D 413/14* (2006.01)
*A61K 31/5377* (2006.01)

(52) U.S. Cl. ..................................... 514/235.5; 544/131
(58) Field of Classification Search .................. 544/131; 514/235.5
See application file for complete search history.

(56) References Cited

U.S. PATENT DOCUMENTS

| | | | |
|---|---|---|---|
| 6,407,120 B1 | 6/2002 | Carpino et al. | |
| 7,812,020 B2 * | 10/2010 | Tornoe et al. | 514/235.5 |
| 2001/0049444 A1 * | 12/2001 | McNaughton-Smith et al. | 546/268.1 |

FOREIGN PATENT DOCUMENTS

| | | |
|---|---|---|
| EP | 554543 | 8/1993 |
| JP | 2003-206230 | 7/2003 |
| WO | 97/15300 | 5/1997 |
| WO | 01/10380 | 2/2001 |
| WO | 01/22953 | 4/2001 |
| WO | 01/92526 | 12/2001 |
| WO | 01/96540 | 12/2001 |
| WO | 02/49628 | 6/2002 |
| WO | 02/066036 | 8/2002 |
| WO | 2004/082677 | 9/2004 |
| WO | 2005/087754 | 9/2005 |

OTHER PUBLICATIONS

Web MD entry for Bipolar Disorder—Prevention (http://www.webmd.com/bipolar-disorder/tc/bipolar-disorder-prevention, accessed Dec. 14, 2011).*
Web MD entry for Epilepsy—Prevention (http://www.webmd.com/epilepsy/tc/epilepsy-prevention, accessed Dec. 14, 2011).*
Jentsch, T.J. Nature Reviews 2000, 1, pp. 21-30.
Wu et al., Biorg. Med. Chem. Lett. 2004, 14, pp. 4533-4537.
Albericio, F., et al. Coupling Reagents and Activation. In Methods in Enzymology: Solid-Phase Peptide Synthesis. New York: Academic Press. 1997. pp. 104-126.
Berge, S. M., et al. Pharmaceutical Salts. Journal of Pharmaceutical Sciences. 1977. 66(1):1-19.
Bialer, M., et al. Progress Report on New Antiepileptic Drugs: A Summary of the Sixth Eilat Conference (EILAT VI). Epilepsy Research. 2002. 51:31-71.
Blackburn-Munro, G., et al. The Anticonvulsant Retigabine Attenuates Nociceptive Behaviours in Rat Models of Persistent and Neuropathic Pain. European Journal of Pharmacology. 2003. 460:109-116.
Bundgaard, H. ed. Designs of Prodrugs. New York: Elsevier. 1985.
Capacio, B. R., et al. Use of the Accelerating Rotarod for Assessment of Motor Performance Decrement Induced by Potential Anticonvulsant Compounds in Nerve Agent Poisoning. Drug and Chemical Toxicology. 1992. 15(3):177-201.
Casser, L. A New Nickel-Catalyzed Synthesis of Aromatic Nitriles. Journal of Organometallic Chemistry. 1973. 54: C57-C58.
Clark, W. M., et al. A Highly Enantioselective Conjugate Reduction of 3-Arylinden-1-ones Using Bakers' Yeast for the Preparation of (S)-3-Arylindan-1-ones. Organic Letters. 1999. 1(11):1839-1842.
Clark, W. M., et al. A Catalytic Enantioselective Synthesis of the Endothelin Receptor Antagonists SB-209670 and SB-217242. A Base-Catalyzed Stereospecific Formal 1,3-Hydrogen Transfer of a Chiral 3-Arylindenol. J. Am. Chem. Soc. 1998. 120:4550-4551.
Cooper, E. C., et al. M-Channels: Neurological Diseases, Neuromodulation, and Drug Development. Arch. Neurol. 2003. 60(4):496-500.

(Continued)

*Primary Examiner* — Joseph Kosack
*Assistant Examiner* — Matthew Coughlin
(74) *Attorney, Agent, or Firm* — Stephen G. Kalinchak; Mary Catherine Di Nunzio; Kitae Lim

(57) ABSTRACT

The present invention relates to pyridine derivatives of the general formula (I) and their use as openers of the KCNQ family potassium ion channels for the treatment of CNS disorders.

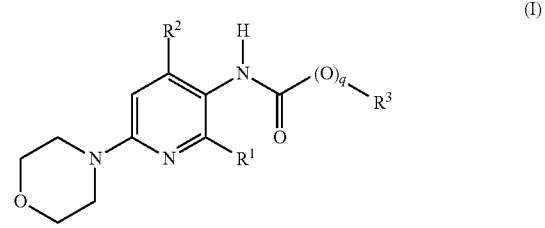

(I)

18 Claims, No Drawings

OTHER PUBLICATIONS

Cooper, E. C., et al. M Channel KCNQ2 Subunits Are Localized to Key Sites for Control of Neuronal Network Oscillations and Synchronization in Mouse Brain. The Journal of Neuroscience. 2001. 21(24):9529-9540.

Cooper, E. C., et al. Colocalization and Coassembly of Two Human Brain M-Type Potassium Channel Subunits That Are Mutated in Epilepsy. Proceedings of the National Academy of Sciences USA. 2000. 97(9):4914-4919.

de la Mare, P.B.D., et al. Preparative Methods of Nitration, in Aromatic Substitution. London: Butterworths Scientific Publications. 1959. pp. 48-56.

Dohle, W., et al. Copper-Mediated Cross-Coupling of Functionalized Arylmagnesium Reagents with Functionalized Alkyl and Benzylic Halides. Organic Letters. 2001. 3(18):2871-2873.

Ebert, U., et al. Delayed Sclerosis, Neuroprotection, and Limbic Epileptogenesis After Status Epilepticus in the Rat. Epilepsia. 2002. 43(Suppl. 5):86-95.

Gennaro, Alfonso, R. ed. Remington: The Science and Practice of Pharmacy. 19th Edition. Mack Publishing Co. Easton, PA. 1995.

Goldstein, M.E., et al. Localization of KCNQ and KCNE Channel Subunits in the Central and Peripheral Nervous System of the Rat. Program No. 53.8. 2003 Abstract Viewer/Itinerary Planner. Washington, DC: Society for Neuroscience, 2003. Online.

Greene, T.W., et al. Protective groups in organic synthesis. 2nd ed. Hoboken, NJ: Wiley Interscience. 1991.

Hamill O. P., et al. Improved Patch-Clamp Techniques for High-Resolution Current Recording From Cells and Cell-Free Membrane Patches. Pflugers Arch. 1981. 391:85-100.

Hartz. B. P., et al. The KCNQ Channel Opener Retigabine Has Anxiolytic Properties. [Abstract] Journal of Psychopharmacology. 2003. 17(suppl 3):A28, B14.

Jacques, J., et al. Enantiomers, Racemates and Resolutions. New York: John Wiley & Sons. 1981.

Jensen, B.S. BMS-204352: A Potassium Channel Opener Developed for the Treatment of Stroke. CNS Drug Rev. 2002. 8(4):353-60.

Jentsch, T. J. Neuronal KCNQ Potassium Channels: Physiology and Role in Disease. Nature Reviews Neuroscience. 2000. 1:21-30.

Keeney, A. J., et al. Alterations in Core Body Temperature, Locomotor Activity, and Corticosterone Following Acute and Repeated Social Defeat of Male NMRI Mice. Physiology and Behaviour. 2001. 74:177-184.

Kimball, A.W., et al. Chemical Protection Against Ionizing Radiation: I. Sampling Methods for Screening Compounds in Radiation Protection Studies With Mice. Radiation Research. 1957. 7:1-12.

Kubisch, C., et al. KCNQ4, A Novel Potassium Channel Expressed in Sensory Outer Hair Cells, Is Mmutated in Dominant Deafness. Cell. 1999. 96(3):437-446.

Lecocq J. Quelques Nouveaux Derives de la p-Amino-Benzene-Sulfonylamide et de la 4-4'-Diamino-Diphenyl Sulfone. Bull. Soc. Chim. Fr. 1950. 46:188-192. [w/ Eng. Abstract].

Lerche, C., et al. Molecular Cloning and Functional Expression of KCNQ5, A Potassium Channel Subunit That May Contribute to Neuronal M-Current Diversity. J Biol Chem. 2000. 275(29):22395-22400.

Marrion, Neil V. Control of M-Current. Annual Review of Physiology. 1997. 59:483-504.

Mitsunobu, O. The Use of Diethyl Azodicarboxylate and Triphenylphosphine in Synthesis and Transformation of Natural Products. Synthesis. Jan. 1981. pp. 1-28.

Mongin F., et al. Advances in the Directed Metallation of Azines and Diazines (Pyridines, Pyrimidines, Pyrazines, Pyridazines, Quinolines, Benzodiazines and Carbolines). Part 1: Metallation of Pyridines, Quinolines and Carbolines. Tetrahedron. 2001. 57:4059-4090.

Negishi, E.-I., et al. The Ortho Lithiation of Tertiary Benzamides. J. Org. Chem. 1977. 42(10):1823-1824.

Noda, M., et al. KCN Channels in Glial Cells. Program No. 53.9. 2003 Abstract Viewer/Itinerary Planner. Washington, DC: Society for Neuroscience, 2003. Online.

Nutt, D.J., et al. Optimizing the Pentetrazol Infusion Test for Seizure Threshold Measurement. J. Pharm. Pharmacol. 1986. 38:697-698.

Racine, R. J. Modification of Seizure Activity by Electrical Stimulation: II. Motor Seizure. Electroencephalography and Clinical Neurophysiology. 1972. 32:281-294.

Robbins, J. KCNQ Potassium Channels: Physiology, Pathophysiology, and Pharmacology. Pharmacology & Therapeutics. 2001. 90:1-19.

Rogawski, M. A. KCNQ2/KCNQ3 K+ Channels and the Molecular Pathogenesis of Epilepsy: Implications for Therapy. Trends in Neurosciences. 2000. 23(9):393-398.

Rostock, A., et al. D-23129: A New Anticonvulsant With a Broad Spectrum Activity in Animal Models of Epileptic Seizures. Epilepsy Research. 1996. 23:211-223.

Saganich, M. J. et al. Differential Expression of Genes Encoding Subthreshold-Operating Voltage-Gated K+ Channels in Brain. Journal of Neuroscience. 2001. 21(13):4609-4624.

Schroder, R. L., et al. Voltage-Independent KCNQ4 Currents Induced by (±) BMS-204352. Pflugers Arch.—European J. Physiology. 2003. 446(5):607-616.

Schroder,R. L., et al. KCNQ4 Channel Activation by BMS-204352 and Retigabine. Neuropharmacology. 2001. 40:888-898.

Siegel, S. Heterogeneous Catalytic Hydrogenation of C=C and Alkynes. In Comprehensive Organic Synthesis. New York: Pergamon Press. 1991. 8:417-442.

Sonogashira, K., et al. A Convenient Synthesis of Acetylenes: Catalytic Substitutions of Acetylenic Hydrogen With Bromoalkenes, Iodoarenes, and Bromopyridines. Tet. Lett. 1975. 16(50):4467-4470.

Starr, M. S., et al. Paradoxical Facilitation of Pilocarpine-Induced Seizures In The Mouse by MK-801 and the Nitric Oxide Synthesis Inhibitor L-NAME. Pharmacology Biochemistry and Behavior. 1993. 45:321-325.

Tang, W., et al. Development and Evaluation of High Throughput Functional Assay Methods for hERG Potassium Channel. J. Biomol. Screen. 2001. 6(5):325-331.

Tatulian, L., et al. Activation of Expressed KCNQ Potassium Currents and Native Neuronal M-Type Potassium Currents by the Anti-Convulsant Drug Retigabine. J Neuroscience. 2001. 21(15):5535-5545.

Tober, C., et al. D-23129: A Potent Anticonvulsant in the Amygdala Kindling Model of Complex Partial Seizures. European Journal of Pharmacology. 1996. 303:163-169.

Wang, H.S., et al. KCNQ2 and KCNQ3 Potassium Channel Subunits: Molecular Correlates of the M-Channel. Science. 1998. 282:1890-1893.

Watson, W. P., et al. The Novel Anticonvulsant, Gabapentin, Protects Against Both Convulsant and Anxiogenic Aspects of the Ethanol Withdrawal Syndrome. Neuropharmacology. 1997. 36(10):1369-1375.

Wickenden, A.D., et al. KCNQ Channel Expression in Rat DRG Following Nerve Ligation. Program No. 454.7. 2002 Abstract Viewer/Itinerary Planner. Washington, DC: Society for Neuroscience, 2002. Online.

Wickenden, A.D., et al. Retigabine, A Novel Anti-Convulsant, Enhances Activation of KCNQ2/Q3 Potassium Channels. Molecular Pharmacology. 2000. 58:591-600.

Wlaz, P., et al. Frontal Versus Transcorneal Stimulation to Induce Maximal Electroshock Seizures or Kindling in Mice and Rats. Epilepsy Research. 1998. 30:219-229.

Yun, J., et al. Efficient Kinetic Resolution in the Asymmetric Hydrosilylation of Imines of 3-Substituted Indanones and 4-Substituted Tetralones. J. Org. Chem. 2000. 65(3):767-774.

International Search Report, International Application No. PCT/DK2006/000123, Jun. 22, 2006.

Jentsch, T.J., Nature Reviews 2000, 1, pp. 21-30; in U.S. Appl. No. 11/817,340.

Wu et al., Bioorg. Med. Chem. Lett. 2004, 14, p. 4533-4537; in U.S. Appl. No. 11/817,340.

Casser, L. A New Nickel-Catalyzed Synthesis of Aromatic Nitriles. Journal of Organometallic Chemistry. 1973. 54:C57-C58.

* cited by examiner

SUBSTITUTED PYRIDINE DERIVATIVES

FIELD OF THE INVENTION

The present invention relates to compounds, which are openers of the KCNQ family potassium ion channels. The compounds are useful in the treatment of disorders and diseases being responsive to opening of the KCNQ family potassium ion channels, one such disease is epilepsy.

BACKGROUND OF THE INVENTION

Ion channels are cellular proteins that regulate the flow of ions, including potassium, calcium, chloride and sodium into and out of cells. Such channels are present in all animal and human cells and affect a variety of processes including neuronal transmission, muscle contraction, and cellular secretion.

Humans have over 70 genes encoding potassium channel subtypes (Jentsch *Nature Reviews Neuroscience* 2000, 1, 21-30) with a great diversity with regard to both stucture and function. Neuronal potassium channels, which are found in the brain, are primarily responsible for maintaining a negative resting membrane potential, as well as controlling membrane repolarisation following an action potential.

One subset of potassium channel genes is the KCNQ family. Mutations in four out of five KCNQ genes have been shown to underlie diseases including cardiac arrhythmias, deafness and epilepsy (Jentsch *Nature Reviews Neuroscience* 2000, 1, 21-30).

The KCNQ4 gene is thought to encode the molecular correlate of a potassium channel found in outer hair cells of the cochlea and in Type I hair cells of the vestibular apparatus, in which, mutations can lead to a form of inherited deafness.

KCNQ1 (KvLQT1) is co-assembled with the product of the KCNE1 (minimal K(+)-channel protein) gene in the heart to form a cardiac-delayed rectifier-like K(+) current. Mutations in this channel can cause one form of inherited long QT syndrome type 1 (LQT1), as well as being associated with a form of deafness (Robbins *Pharmacol Ther* 2001, 90, 1-19).

The genes KCNQ2 and KCNQ3 were discovered in 1988 and appear to be mutated in an inherited form of epilepsy known as benign familial neonatal convulsions (Rogawski *Trends in Neurosciences* 2000, 23, 393-398). The proteins encoded by the KCNQ2 and KCNQ3 proteins are localised in the pyramidal neurons of the human cortex and hippocampus, regions of the brain associated with seizure generation and propagation (Cooper et al. *Proceedings National Academy of Science USA* 2000, 97, 4914-4919).

KCNQ2 and KCNQ3 are two potassium channel subunits that form "M-currents" when expressed in vitro. The M-current is a non-inactivating potassium current found in many neuronal cell types. In each cell type, it is dominant in controlling membrane excitability by being the only sustained current in the range of action potential initiation (Manion *Annual Review Physiology* 1997, 59, 483-504). Modulation of the M-current has dramatic effects on neuronal excitability, for example activation of the current will reduce neuronal excitability. Openers of these KCNQ channels, or activators of the M-current, will reduce excessive neuronal activity and may thus be of use in the treatment of seizures and other diseases and disorders characterised by excessive neuronal activity, such as neuronal hyperexcitability including convulsive disorders, epilepsy and neuropathic pain.

Retigabine (D-23129; N-(2-amino-4-(4-fluorobenzylamino)-phenyl)carbamic acid ethyl ester) and analogues thereof are disclosed in EP554543. Retigabine is an anti-convulsive compound with a broad spectrum and potent anticonvulsant properties, both in vitro and in vivo. It is active after oral and intraperitoneal administration in rats and mice in a range of anticonvulsant tests including: electrically induced seizures, seizures induced chemically by pentylenetetrazole, picrotoxin and N-methyl-D-aspartate (NMDA) and in a genetic animal model, the DBA/2 mouse (Rostock et al. *Epilepsy Research* 1996, 23, 211-223). In addition, retigabine is active in the amygdala kindling model of complex partial seizures, further indicating that this compound has potential for anti-convulsive therapy. In clinical trials, retigabine has recently shown effectiveness in reducing the incidence of seizures in epileptic patients (Bialer et al. *Epilepsy Research* 2002, 51, 31-71).

Retigabine has been shown to activate a K(+) current in neuronal cells and the pharmacology of this induced current displays concordance with the published pharmacology of the M-channel, which recently was correlated to the KCNQ2/3 K(+) channel heteromultimer. This suggests that activation of KCNQ2/3 channels may be responsible for some of the anticonvulsant activity of this agent (Wickenden et al. *Molecular Pharmacology* 2000, 58, 591-600)—and that other agents working by the same mechanism may have similar uses.

KCNQ 2 and 3 channels have also been reported to be upregulated in models of neuropathic pain (Wickenden et al. *Society for Neuroscience Abstracts* 2002, 454.7), and potassium channel modulators have been hypothesised to be active in both neuropathic pain and epilepsy (Schroder et al. *Neuropharmacology* 2001, 40, 888-898).

Retigabine has also been shown to be beneficial in animal models of neuropathic pain (Blackburn-Munro and Jensen *European Journal of Pharmacology* 2003, 460, 109-116), and it is thus suggested that openers of KCNQ channels will be of use in treating pain disorders including neuropathic pain.

The localisation of KCNQ channel mRNA is reported in brain and other central nervous system areas associated with pain (Goldstein et al. *Society for Neuroscience Abstracts* 2003, 53.8).

In addition to a role in neuropathic pain, the expression of mRNA for KCNQ 2-5 in the trigeminal and dorsal root ganglia and in the trigeminal nucleus caudalis implies that openers of these channels may also affect the sensory processing of migraine pain (Goldstein et al. *Society for Neuroscience Abstracts* 2003, 53.8).

Recent reports demonstrate that mRNA for KCNQ 3 and 5, in addition to that for KCNQ2, are expressed in astrocytes and glial cells. Thus KCNQ 2, 3 and 5 channels may help modulate synaptic activity in the CNS and contribute to the neuroprotective effects of KCNQ channel openers (Noda et al., *Society for Neuroscience Abstracts* 2003, 53.9).

Retigabine and other KCNQ modulators may thus exhibit protection against the neurodegenerative aspects of epilepsy, as retigabine has been shown to prevent limbic neurodegeneration and the expression of markers of apoptosis following kainic acid-induced status epilepticus in the rat (Ebert et al. *Epilepsia* 2002, 43 Suppl 5, 86-95). This may have relevance for preventing the progression of epilepsy in patients, i.e. be anti-epileptogenic. Retigabine has also been shown to delay the progression of hippocampal kindling in the rat, a further model of epilepsy development (Tober et al. *European Journal Of Pharmacology* 1996, 303, 163-169).

It is thus suggested that these properties of retigabine and other KCNQ modulators may prevent neuronal damage induced by excessive neuronal activation, and such compounds may be of use in the treatment of neurodegenerative diseases, and be disease modifying (or antiepileptogenic) in patients with epilepsy.

Given that anticonvulsant compounds such as benzodiazepines and chlormethiazole are used clincially in the treatment of the ethanol withdrawal syndrome and that other anticonvulsant compounds e.g. gabapentin, are very effective in animal models of this syndrome (Watson et al. *Neuropharmacology* 1997, 36, 1369-1375), other anticonvulsant compounds such as KCNQ openers are thus expected to be effective in this condition.

mRNA for KCNQ 2 and 3 subunits are found in brain regions associated with anxiety and emotional behaviours such as bipolar disorder, e.g., hippocampus and amygdale (Saganich et al. *Journal of Neuroscience* 2001, 21, 4609-4624); and retigabine is reportedly active in some animal models of anxiety-like behaviour (Hartz et al. *Journal of Pyschopharmacology* 2003, 17 suppl. 3, A28, B 14), and other clinically used antconvulsant compounds are used in the treatment of biopolar disorder. Thus, KCNQ openers may be useful for the treatment of anxiety disorders and biopolar disorder.

WO 200196540 discloses the use of modulators of the M-current formed by expression of KCNQ2 and KCNQ3 genes for insomnia, while WO 2001092526 discloses that modulators of KCNQ5 can be utilized for the treatment of sleep disorders.

WO01/022953 describes the use of retigabine for prophylaxis and treatment of neuropathic pain such as allodynia, hyperalgesic pain, phantom pain, neuropathic pain related to diabetic neuropathy and neuropathic pain related to migraine.

WO02/049628 describes the use of retigabine for the treatment of anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

WO97/15300 describes the use of retigabine for the treatment of neurodegenerative disorders such as Alzheimer's disease; Huntington's chorea; sclerosis such as multiple sclerosis and amyotrophic lateral sclerosis; Creutzfeld-Jakob disease; Parkinson's disease; encephalopathies induced by AIDS or infection by rubella viruses, herpes viruses, borrelia and unknown pathogens; trauma-induced neurodegenerations; neuronal hyperexcitation states such as in medicament withdrawal or intoxication; and neurodegenerative diseases of the peripheral nervous system such as polyneuropathies and polyneuritides.

KCNQ channel openers have also been found to be effective in the treatment of stroke, therefore it can be expected that selective KCNQ openers are effective in the treatment of stroke (Schroder et al., Pflugers Arch., 2003; 446(5): 607-16; Cooper and Jan, Arch Neurol., 2003, 60(4):496-500; Jensen, CNS Drug Rev., 2002, 8(4):353-60).

KCNQ channels have been shown to be expressed in dopaminergic and cholinergic circuits in the brain that are associated with the brain's reward system, particularly the ventral tegmental area (Cooper et al., J Neurosci, 2001, 21, 9529-9540). Therefore, KCNQ channel openers are expected to be effective in hyperexcitability disorders that involve the brain's reward system such as cocaine abuse, nicotine withdrawal and ethanol withdrawal.

Potassium channels comprised of the KCNQ4 subunits are expressed in the inner ear (Kubisch et al., Cell., 1999 Feb. 5; 96(3):437-46) and opening of these channels is therefore expected to treat tinnitus.

Hence, there is a great desire for novel compounds which are potent openers of the KCNQ family of potassium channels.

Also desired are novel compounds with improved properties relative to known compounds, which are openers of the KCNQ family potassium channels, such as retigabine.

Improvement of one or more of the following parameters is desired: half-life, clearance, selectivity, interactions with other medications, bioavailability, potency, formulability, chemical stability, metabolic stability, membrane permeability, solubility and therapeutic index. The improvement of such parameters may lead to improvements such as:

an improved dosing regime by reducing the number of required doses a day,
ease of administration to patients on multiple medications,
reduced side effects,
enlarged therapeutic index,
improved tolerability or
improved compliance.

SUMMARY OF THE INVENTION

One object of the invention is the provision of compounds, which are potent openers of the KCNQ family potassium channels.

The compounds of the invention are substituted pyridine derivatives of the below formula I as the free base or a salt thereof

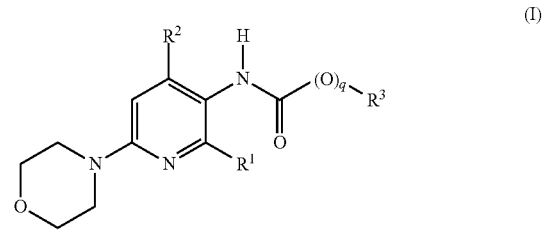

(I)

wherein
$R^1$, $R^2$, $R^3$ and q are as defined below.

The invention provides a compound of formula I for use as a medicament.

The invention provides a pharmaceutical composition comprising a compound of formula I and a pharmaceutically acceptable carrier or diluent.

The invention provides the use of a compound of formula I for the preparation of a medicament for the treatment of seizure disorders, anxiety disorders, neuropathic pain and migraine pain disorders or neurodegenerative disorders.

The invention furthermore concerns the use of a compound of formula I in a method of treatment of seizure disorders, anxiety disorders, neuropathic pain and migraine pain disorders or neurodegenerative disorders.

Definition Substituents

The term "heteroatom" refers to a nitrogen, oxygen or sulphur atom.

"Halogen" means fluoro, chloro, bromo or iodo. "Halo" means halogen.

"Cyano" designates

which is attached to the remainder of the molecule via the carbon atom.

The expression "$C_{1-6}$-alk(en/yn)yl" means $C_{1-6}$-alkyl, $C_{2-6}$-alkenyl or $C_{2-5}$-alkynyl.

The term "$C_{1-6}$-alkyl" refers to a branched or unbranched alkyl group having from one to six carbon atoms, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl, pent-3-yl, hex-1-yl, hex-2-yl and hex-3-yl.

The term "$C_{2-6}$-alkenyl" refers to a branched or unbranched alkenyl group having from two to six carbon atoms and one double bond, including but not limited to ethenyl, propenyl, and butenyl.

The term "$C_{2-6}$-alkynyl" refers to a branched or unbranched alkynyl group having from two to six carbon atoms and one triple bond, including but not limited to ethynyl, propynyl and butynyl.

The expression "$C_{1-8}$-alk(en/yn)yl" means $C_{1-8}$-alkyl, $C_{2-8}$-alkenyl or $C_{2-8}$-alkynyl.

The term "$C_{1-8}$-alkyl" refers to a branched or unbranched alkyl group having from one to eight carbon atoms, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl, pent-3-yl, hex-1-yl, hex-2-yl, hex-3-yl, 2-methyl-4,4-dimethyl-pent-1-yl and hept-1-yl.

The term "$C_{2-8}$-alkenyl" refers to a branched or unbranched alkenyl group having from two to eight carbon atoms and one double bond, including but not limited to ethenyl, propenyl, and butenyl.

The term "$C_{2-8}$-alkynyl" refers to a branched or unbranched alkynyl group having from two to eight carbon atoms and one triple bond, including but not limited to ethynyl, propynyl and butynyl.

The expression "$C_{3-8}$-cycloalk(en)yl" means $C_{3-8}$-cycloalkyl or $C_{3-8}$-cycloalkenyl.

The term "$C_{3-8}$-cycloalkyl" designates a monocyclic or bicyclic carbocycle having three to eight carbon atoms, including but not limited to cyclopropyl, cyclopentyl, cyclohexyl, bicycloheptyl such as 2-bicyclo[2.2.1]heptyl.

The term "$C_{3-8}$-cycloalkenyl" designates a monocyclic or bicyclic carbocycle having three to eight carbon atoms and one double bond, including but not limited to cyclopentenyl and cyclohexenyl.

The term "$C_{3-8}$-heterocycloalk(en)yl" means $C_{3-8}$-heterocycloalkyl or $C_{3-8}$-heterocycloalkenyl.

The term "$C_{3-8}$-heterocycloalkyl" designates a monocyclic or bicyclic ring system wherein the ring is formed by 3 to 8 atoms selected from 2-7 carbon atoms and 1 or 2 heteroatoms independently selected from nitrogen, oxygen and sulphur atoms. Examples of $C_{3-8}$-heterocycloalkyls are pyrrolidine, azepan, morpholine, piperidine, piperazine and tetrahydrofuran.

The term "$C_{3-8}$-heterocycloalkenyl" designates a monocyclic or bicyclic ring system with one double bond, wherein the ring is formed by 3 to 8 atoms selected from 2-7 carbon atoms and 1 or 2 heteroatoms independently selected from nitrogen, oxygen and sulphur atoms. Examples of $C_{3-8}$-heterocycloalkenyls are dihydropyrrole, dihydrofuran and dihydrothiophene.

When $C_{3-8}$-heterocycloalk(en)yl comprises nitrogen then $C_{3-8}$-heterocycloalk(en)yl is attached to the remainder of the molecule via a carbon atom or nitrogen atom of the heterocyclic ring.

When $C_{3-8}$-heterocycloalk(en)yl does not comprise nitrogen then $C_{3-8}$-heterocycloalk(en)yl is attached to the remainder of the molecule via a carbon atom of the heterocyclic ring.

The term "halo-$C_{1-6}$-alk(en/yn)yl" designates $C_{1-6}$-alk(en/yn)yl being substituted with halogen, including but not limited to trifluoromethyl.

Similarly, "halo-$C_{3-8}$-cycloalk(en)yl" designates $C_{3-8}$-cycloalk(en)yl being substituted with halogen, including but not limited to chlorocyclopropane and chlorocyclohexane.

Similarly, "halo-$C_{3-8}$-cycloalk(en)yl-$C_{1-6}$-alk(en/yn)yl" designates halo-$C_{3-8}$-cycloalk(en)yl being attached to the remainder of the molecule via $C_{1-6}$-alk(en/yn)yl.

The term "$C_{1-6}$-alk(en/yn)yloxy" designates $C_{1-6}$-alk(en/yn)yl being attached to the remainder of the molecule via an oxygen atom.

Similarly, "$C_{3-8}$-cycloalk(en)yloxy" designates $C_{3-8}$-cycloalk(en)yl being attached to the remainder of the molecule via an oxygen atom.

In the expressions "$C_{3-8}$-cycloalk(en)yl-$C_{1-6}$-alk(en/yn)yl", "Aryl-$C_{1-6}$-alk(en/yn)yl", "Aryl-$C_{3-8}$-cycloalk(en)yl", "Aryl-$C_{3-8}$-cycloalk(en)yl-$C_{1-6}$-alk(en/yn)yl", "$C_{3-8}$-heterocycloalk(en)yl-$C_{1-6}$-alk(en/yn)yl", "$C_{1-6}$-alk(en/yn)yl-$C_{3-8}$-heterocycloalk(en)yl-$C_{1-6}$-alk(en/yn)yl", "Heteroaryl-$C_{1-6}$-alk(en/yn)yl", "Heteroaryl-$C_{3-8}$-cycloalk(en)yl", "Heteroaryl-$C_{3-8}$-cycloalk(en)yl-$C_{1-6}$-alk(en/yn)yl", "$NR^4R^5$—$C_{1-6}$-alk(en/yn)yl", "$NR^4R^5$—$C_{3-8}$-cycloalk(en)yl", "$NR^4R^5$—$C_{3-8}$-cycloalk(en)yl-$C_{1-6}$-alk(en/yn)yl", "$C_{3-5}$-cycloalk(en)yl-$C_{1-6}$-alk(en/yn)yloxy", "$C_{1-6}$-alk(en/yn)yloxy-$C_{1-6}$-alk(en/yn)yl", "$C_{3-8}$-cycloalk(en)yloxy-$C_{1-6}$-alk(en/yn)yl" and "$C_{3-8}$-cycloalk(en)yl-$C_{1-6}$-alk(en/yn)yloxy-$C_{1-6}$-alk(en/yn)yl" the terms "$C_{1-6}$-alk(en/yn)yl", "$C_{3-8}$-cycloalk(en)yl", "Aryl", "$C_{3-8}$-heterocycloalk(en)yl", "Heteroaryl", "$C_{1-6}$-alk(en/yn)yloxy" and "$C_{3-8}$-cycloalk(en)yloxy" are as defined above.

The term "Heteroaryl" refers to monocyclic or bicyclic heteroaromatic systems being selected from the group consisting of pyridine, thiophene, furan, pyrrole, pyrazole, triazole, tetrazole, oxazole, imidazole, thiazole, benzofuran, benzothiophene and indole.

The term Aryl designates monocyclic or bicyclic aromatic systems being selected from the group consisting of phenyl and naphthyl.

The term "optionally substituted Aryl-$C_{1-6}$-alk(en/yn)yl" designates Aryl-$C_{1-6}$-alk(en/yn)yl wherein the Aryl moiety is optionally substituted, such as with 1, 2 or 3 substituents independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy.

Similarly, "optionally substituted Aryl-$C_{3-8}$-cycloalk(en)yl" designates Aryl-$C_{3-8}$-cycloalk(en)yl wherein the Aryl moiety is optionally substituted, such as with 1, 2 or 3 substituents independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy.

Similarly, "optionally substituted Aryl-$C_{3-8}$-cycloalk(en)yl-$C_{1-6}$-alk(en/yn)yl" designates Aryl-$C_{3-8}$-cycloalk(en)yl-$C_{1-6}$-alk(en/yn)yl wherein the Aryl moiety is optionally substituted, such as with 1, 2 or 3 substituents independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy.

DESCRIPTION OF THE INVENTION

The present invention relates to substituted pyridine derivatives which are openers of KCNQ potassium channels.

The present invention relates to a compound represented by the general formula I:

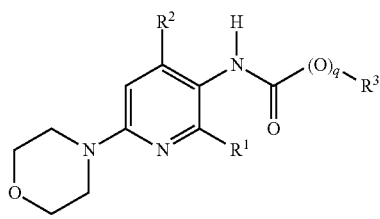

wherein
q is 0 or 1;
each of $R^1$ and $R^2$ is independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy; and $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, optionally substituted Aryl-$C_{1-6}$-alk(en/yn)yl, optionally substituted Aryl-$C_{3-8}$-cycloalk(en)yl, optionally substituted Aryl-$C_{3-8}$-cycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, Heteroaryl-$C_{1-6}$-alk(en/yn)yl, Heteroaryl-$C_{3-8}$-cycloalk(en)yl, Heteroaryl-$C_{3-8}$-cycloalk(en)yl-$C_{1-6}$-alk(en/yn)yl, $NR^4R^5$—$C_{1-6}$-alk(en/yn)yl, $NR^4R^5$—$C_{3-8}$-cycloalk(en)yl, $NR^4R^5$—$C_{3-8}$-cycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl; wherein
each of $R^4$ and $R^5$ is independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;
as the free base or salts thereof.

In one embodiment of the compound of formula I, q is 0;
in another embodiment of the compound of formula I, q is 1.

In a further embodiment of the compound of formula I each of $R^1$ and $R^2$ is independently selected from the group consisting of halogen, cyano, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy;

in another embodiment each of $R^1$ and $R^2$ is independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy;

in another embodiment each of $R^1$ and $R^2$ is independently selected from the group consisting of halogen, cyano and $C_{1-6}$-alk(en/yn)yl and $C_{1-6}$-alk(en/yn)yloxy;

in another embodiment each of $R^1$ and $R^2$ is independently selected from the group consisting of $C_{1-6}$-alk(en/yn)yl, $C_{3-8}$-cycloalk(en)yl and $C_{3-8}$-cycloalk(en)yl-$C_{1-6}$-alk(en/yn)yl;

in another embodiment $R^1$ is $C_{1-6}$-alk(en/yn)yl, such as methyl;
in another embodiment $R^2$ is $C_{1-6}$-alk(en/yn)yl, such as methyl;
in another embodiment $R^1$ is $C_{1-6}$-alk(en/yn)yloxy, such as methoxy and $R^2$ is halogen;
in another embodiment $R^1$ is halogen and $R^2$ is $C_{1-6}$-alk(en/yn)yloxy, such as methoxy.

Typically, both $R^1$ and $R^2$ are $C_{1-6}$-alk(en/yn)yl, such as methyl.

In a further embodiment of the compound of formula I, $R^3$ is selected from the group consisting of $C_{1-6}$-alk(en/yn)yl-$C_{3-8}$-heterocycloalk(en)yl-$C_{1-6}$-alk(en/yn)yl, $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, $NR^4R^5$—$C_{1-6}$-alk(en/yn)yl, $NR^4R^5$—$C_{3-8}$-cycloalk(en)yl, $NR^4R^5$—$C_{3-8}$-cycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl;

in another embodiment $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, optionally substituted Aryl-$C_{1-6}$-alk(en/yn)yl, optionally substituted Aryl-$C_{3-8}$-cycloalk(en)yl, optionally substituted Aryl-$C_{3-8}$-cycloalk(en)yl-$C_{1-6}$-alk(en/yn)yl, Heteroaryl-$C_{1-6}$-alk(en/yn)yl, Heteroaryl-$C_{3-8}$-cycloalk(en)yl, Heteroaryl-$C_{3-8}$-cycloalk(en)yl-$C_{1-6}$-alk(en/yn)yl, $NR^4R^5$—$C_{1-6}$-alk(en/yn)yl, $NR^4R^5$—$C_{3-8}$-cycloalk(en)yl and $NR^4R^5$—$C_{3-8}$-cycloalk(en)yl-$C_{1-6}$-alk(en/yn)yl;

in another embodiment $R^3$ is selected from the group consisting of $C_{1-8}$-alk(en/yn)yl, $C_{3-8}$-cycloalk(en)yl-$C_{1-6}$-alk(en/yn)yl, optionally substituted Aryl-$C_{1-6}$-alk(en/yn)yl, optionally substituted Aryl-$C_{3-8}$-cycloalk(en)yl, Heteroaryl-$C_{1-6}$-alk(en/yn)yl and $NR^4R^5$—$C_{1-6}$-alk(en/yn)yl;

in another embodiment $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, optionally substituted Aryl-$C_{1-6}$-alk(en/yn)yl, optionally substituted Aryl-$C_{3-8}$-cycloalk(en)yl, optionally substituted Aryl-$C_{3-8}$-cycloalk(en)yl-$C_{1-6}$-alk(en/yn)yl, Heteroaryl-$C_{1-6}$-alk(en/yn)yl, Heteroaryl-$C_{3-8}$-cycloalk(en)yl and Heteroaryl-$C_{3-8}$-cycloalk(en)yl-$C_{1-6}$-alk(en/yn)yl.

Typically, $R^3$ is selected from the group consisting of $C_{1-8}$-alk(en/yn)yl, $C_{3-8}$-cycloalk(en)yl-$C_{1-6}$-alk(en/yn)yl, optionally substituted Aryl-$C_{1-6}$-alk(en/yn)yl, optionally substituted Aryl-$C_{3-8}$-cycloalk(en)yl and Heteroaryl-$C_{1-6}$-alk(en/yn)yl.

To further illustrate without limiting the invention, an embodiment of $R^3$ is $C_{1-8}$-alk(en/yn)yl;
another embodiment of $R^3$ is $C_{3-8}$-cycloalk(en)yl-$C_{1-6}$-alk(en/yn)yl;
another embodiment of $R^3$ is optionally substituted Aryl-$C_{1-6}$-alk(en/yn)yl;
another embodiment of $R^3$ is optionally substituted Aryl-$C_{3-8}$-cycloalk(en)yl;
another embodiment of $R^3$ is Heteroaryl-$C_{1-6}$-alk(en/yn)yl.

In a further embodiment of the compound of formula I, each of $R^4$ and $R^5$ is independently selected from the group consisting of $C_{3-8}$-cycloalk(en)yl and $C_{3-8}$-cycloalk(en)yl-$C_{1-6}$-alk(en/yn)yl;

in another embodiment each of $R^4$ and $R^5$ is independently selected from the group consisting of $C_{1-6}$-alk(en/yn)yl and hydrogen;

in another embodiment both $R^4$ and $R^5$ are $C_{1-6}$-alk(en/yn)yl;

in another embodiment both $R^4$ and $R^5$ are hydrogen.

In a further embodiment of the compound of formula I, any Heteroaryl, which is mentioned either alone or as a part of a larger substituent is selected form the group consisting of pyridine, furan, pyrrole, pyrazole, triazole, tetrazole, oxazole, imidazole, thiazole, benzofuran, benzothiophene and indole; in another embodiment any Heteroaryl, which is mentioned either alone or as a part of a larger substituent is thiophene.

In a further embodiment of the compound of formula I, any Aryl, which is mentioned either alone or as a part of a larger substituent is phenyl;

in another embodiment any Aryl, which is mentioned either alone or as a part of a larger substituent is naphthyl.

In a further embodiment of the compound of formula I, any optionally substituted Aryl, which is mentioned either alone or as a part of a larger substituent, may be substituted with 1 or 2 substituents.

To further illustrate without limiting the invention an embodiment concerns such compounds of formula I, wherein any optionally substituted Aryl which is mentioned either alone or as a part of a larger substituent is not substituted;

in another embodiment any optionally substituted Aryl which is mentioned either alone or as a part of a larger substituent is substituted with 1 substituent;

in another embodiment any optionally substituted Aryl which is mentioned either alone or as a part of a larger substituent is substituted with 2 substituents.

In a further embodiment of the compound of formula I, any optionally substituted Aryl, which is mentioned either alone or as a part of a larger substituent, may be substituted with substituents selected from the group consisting of cyano, $C_{3-8}$-cycloalk(en)yl, $C_{3-8}$-cycloalk(en)yl-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{3-8}$-cycloalk(en)yloxy and $C_{3-8}$-cycloalk(en)yl-$C_{1-6}$-alk(en/yn)yloxy;

in another embodiment any optionally substituted Aryl which is mentioned either alone or as a part of a larger substituent may be substituted with substituents selected from the group consisting of halogen, $C_{1-6}$-alk(en/yn)yl, halo-$C_{1-6}$-alk(en/yn)yl and $C_{1-6}$-alk(en/yn)yloxy.

To further illustrate without limiting the invention an embodiment concerns such compounds of formula I, wherein any optionally substituted Aryl which is mentioned either alone or as a part of a larger substituent is substituted with halogen;

in another embodiment any optionally substituted Aryl which is mentioned either alone or as a part of a larger substituent is substituted with $C_{1-6}$-alk(en/yn)yl;

in another embodiment any optionally substituted Aryl which is mentioned either alone or as a part of a larger substituent is substituted with halo-$C_{1-6}$-alk(en/yn)yl;

in another embodiment any optionally substituted Aryl which is mentioned either alone or as a part of a larger substituent is substituted with $C_{1-6}$-alk(en/yn)yloxy.

A further embodiment concerns a compound of formula I as the free base or a salt thereof, said compound is selected from the compounds of the following scheme.

| Example No. | Compound name |
| --- | --- |
| 1aa | (2,4-Dimethyl-6-morpholin-4-yl-pyridin-3-yl)-carbamic acid benzyl ester |
| 1ab | (2,4-Dimethyl-6-morpholin-4-yl-pyridin-3-yl)-carbamic acid 2-chloro-benzyl ester |
| 1ac | 2-(4-Chloro-phenyl)-N-(2,4-dimethyl-6-morpholin-4-yl-pyridin-3-yl)-acetamide |
| 1ad | 2-Phenyl-cyclopropanecarboxylic acid (2,4-dimethyl-6-morpholin-4-yl-pyridin-3-yl)-amide |
| 1ae | N-(2,4-Dimethyl-6-morpholin-4-yl-pyridin-3-yl)-2-thiophen-2-yl-acetamide |
| 1af | 3-Cyclohexyl-N-(2,4-dimethyl-6-morpholin-4-yl-pyridin-3-yl)-propionamide |
| 1ag | (2,4-Dimethyl-6-morpholin-4-yl-pyridin-3-yl)-carbamic acid isobutyl ester |
| 1ah | 3-(3-Chloro-phenyl)-N-(2,4-dimethyl-6-morpholin-4-yl-pyridin-3-yl)-propionamide |
| 1ai | N-(2,4-Dimethyl-6-morpholin-4-yl-pyridin-3-yl)-2-(3,5-dimethyl-phenyl)-acetamide |
| 1aj | N-(2,4-Dimethyl-6-morpholin-4-yl-pyridin-3-yl)-3-p-tolyl-propionamide |
| 1ak | 2-(3-Chloro-phenyl)-N-(2,4-dimethyl-6-morpholin-4-yl-pyridin-3-yl)-acetamide |
| 1al | 2-(3,4-Dichloro-phenyl)-N-(2,4-dimethyl-6-morpholin-4-yl-pyridin-3-yl)-acetamide |
| 1am | N-(2,4-Dimethyl-6-morpholin-4-yl-pyridin-3-yl)-2-thiophen-3-yl-acetamide |
| 1an | N-(2,4-Dimethyl-6-morpholin-4-yl-pyridin-3-yl)-2-p-tolyl-acetamide |
| 1ao | 2-(3-Bromo-phenyl)-N-(2,4-dimethyl-6-morpholin-4-yl-pyridin-3-yl)-acetamide |
| 1ap | N-(2,4-Dimethyl-6-morpholin-4-yl-pyridin-3-yl)-2-(3-trifluoromethyl-phenyl)-acetamide |
| 1aq | N-(2,4-Dimethyl-6-morpholin-4-yl-pyridin-3-yl)-2-phenyl-acetamide |
| 1ar | 3,5,5-Trimethyl-hexanoic acid (2,4-dimethyl-6-morpholin-4-yl-pyridin-3-yl)-amide |
| 1as | Octanoic acid (2,4-dimethyl-6-morpholin-4-yl-pyridin-3-yl)-amide |
| 1at | N-(2,4-Dimethyl-6-morpholin-4-yl-pyridin-3-yl)-2-naphthalen-2-yl-acetamide |
| 1au | Heptanoic acid (2,4-dimethyl-6-morpholin-4-yl-pyridin-3-yl)-amide |
| 1av | N-(2,4-Dimethyl-6-morpholin-4-yl-pyridin-3-yl)-2-(3,4-dimethyl-phenyl)-acetamide |
| 1aw | 2-(Cyclohex-1-enyl)-N-(2,4-dimethyl-6-morpholin-4-yl-pyridin-3-yl)-acetamide |
| 1ax | N-(2,4-Dimethyl-6-morpholin-4-yl-pyridin-3-yl)-2-(4-methoxy-3-methyl-phenyl)-acetamide |
| 1ay | N-(2,4-Dimethyl-6-morpholin-4-yl-pyridin-3-yl)-2-(4-methoxy-phenyl)-acetamide |
| 1az | N-(2,4-Dimethyl-6-morpholin-4-yl-pyridin-3-yl)-3-(4-methoxy-phenyl)-propionamide |
| 1ba | N-(2,4-Dimethyl-6-morpholin-4-yl-pyridin-3-yl)-2-m-tolyl-acetamide |
| 1bb | N-(2,4-Dimethyl-6-morpholin-4-yl-pyridin-3-yl)-2-(4-fluoro-phenyl)-acetamide |
| 1bc | N-(2,4-Dimethyl-6-morpholin-4-yl-pyridin-3-yl)-3,3-dimethyl-butyramide |
| 1bd | N-(2,4-Dimethyl-6-morpholin-4-yl-pyridin-3-yl)-2-(3-fluoro-phenyl)-acetamide |
| 1be | 2-Bicyclo[2.2.1]hept-2-yl-N-(2,4-dimethyl-6-morpholin-4-yl-pyridin-3-yl)-acetamide |
| 1bf | 2-(3,4-Difluoro-phenyl)-N-(2,4-dimethyl-6-morpholin-4-yl-pyridin-3-yl)-acetamide |
| 1bg | 4-Methyl-pentanoic acid (2,4-dimethyl-6-morpholin-4-yl-pyridin-3-yl)-amide |
| 1bh | 2-(Cyclopent-2-enyl)-N-(2,4-dimethyl-6-morpholin-4-yl-pyridin-3-yl)-acetamide |
| 1bi | 2-Cyclohexyl-N-(2,4-dimethyl-6-morpholin-4-yl-pyridin-3-yl)-acetamide |
| 1bj | 5-Methyl-hexanoic acid (2,4-dimethyl-6-morpholin-4-yl-pyridin-3-yl)-amide |
| 1bk | 2-Cyclopentyl-N-(2,4-dimethyl-6-morpholin-4-yl-pyridin-3-yl)-acetamide |

-continued

| Example No. | Compound name |
|---|---|
| 1bl | 3-Cyclopentyl-N-(2,4-dimethyl-6-morpholin-4-yl-pyridin-3-yl)-propionamide |
| 1bm | Hexanoic acid (2,4-dimethyl-6-morpholin-4-yl-pyridin-3-yl)-amide |
| 1bn | N-(4-Chloro-2-methoxy-6-morpholin-4-yl-pyridin-3-yl)-2-cyclopentylacetamide |
| 1bo | N-(2-Chloro-4-methoxy-6-morpholin-4-yl-pyridin-3-yl)-2-cyclopentylacetamide |
| 1bp | N-(2-Chloro-4-methoxy-6-morpholin-4-yl-pyridin-3-yl)-3,3-dimethylbutyramide |
| 1bq | N-(4-Chloro-2-methoxy-6-morpholin-4-yl-pyridin-3-yl)-3,3-dimethylbutyramide |
| 1br | N-(4-Chloro-2-methoxy-6-morpholin-4-yl-pyridin-3-yl)-propionamide |

Each of these compounds is considered a specific embodiment and may be subjected to individual claims.

The present invention also comprises salts of the compounds of the invention, typically, pharmaceutically acceptable salts. The salts of the invention include acid addition salts, metal salts, ammonium and alkylated ammonium salts.

The salts of the invention are preferably acid addition salts. The acid addition salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977,66,2, which is incorporated herein by reference.

Also intended as acid addition salts are the hydrates, which the present compounds, are able to form.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centre and it is intended that any optical isomers (i.e. enantiomers or diastereomers), as separated, pure or partially purified optical isomers and any mixtures thereof including racemic mixtures, i.e. a mixture of stereoisomers, are included within the scope of the invention.

Racemic forms can be resolved into the optical antipodes by known methods, for example, by separation of diastereomeric salts with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, or by stereoselective synthesis.

Furthermore, when a double bond or a fully or partially saturated ring system is present in the molecule, geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula I, which are readily convertible in vivo into the required compound of the formula I. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the invention have affinity for the KCNQ2 receptor subtype with an $EC_{50}$ of less than 15000 nM such as less than 10000 nM as measured by the test "Relative efflux through the KCNQ2 channel" which is described below. One embodiment concerns such compounds of formula I having affinity for the KCNQ2 receptor subtype with an $EC_{50}$ of less than 2000 nM such as less than 1500 nM as measured by the test "Relative efflux through the KCNQ2 channel" which is described below. To further illustrate without limiting the invention an embodiment concerns such compounds having affinity for the KCNQ2 receptor subtype with an $EC_{50}$ of less than 200 nM such as less than 150 nM as measured by the test "Relative efflux through the KCNQ2 channel" which is described below.

One embodiment concerns such compounds of formula I having an $ED_{50}$ of less than 15 mg/kg in the test "Maximum electroshock" which is described below. To further illustrate without limiting the invention, an embodiment concerns such compounds having an $ED_{50}$ of less than 5 mg/kg in the test "Maximum electroshock" which is described below.

One embodiment concerns such compounds of formula I having an $ED_{50}$ of less than 5 mg/kg in the "Electrical seizure -threshold test" and "Chemical seizure -threshold test" which is described below.

One embodiment concerns such compounds of formula I having few or clinically insignificant side effects. Some of the compounds according to the invention are thus tested in models of the unwanted sedative, hypothermic and ataxic actions.

One embodiment concerns such compounds of formula I having a large therapeutic index between anticonvulsant efficacy and side-effects such as impairment of locomotor activity or ataxic effects as measured by performance on a rotating rod. Such compounds will expectedly be well tolerated in patients permitting high doses to be used before side effects are seen. Thereby compliance with the therapy will expectedly be good and administration of high doses may be permitted making the treatment more efficacious in patients who would otherwise have side effects with other medications.

As already mentioned, the compounds according to the invention have effect on potassium channels of the KCNQ family, in particular the KCNQ2 subunit, and they are thus considered useful for increasing ion flow in a voltage-dependent potassium channel in a mammal such as a human. The compounds of the invention are considered applicable in the treatment of a disorder or disease being responsive to an increased ion flow in a potassium channel such as the KCNQ family potassium ion channels. Such disorder or disease is preferably a disorder or disease of the central nervous system.

In one aspect, the compounds of the invention may be administered as the only therapeutically effective compound.

In another aspect the compounds of the invention may be administered as a part of a combination therapy, i.e. the compounds of the invention may be administered in combination with other therapeutically effective compounds having e.g. anti-convulsive properties. The effects of such other compounds having anti-convulsive properties may include but not be limited to activities on:
- ion channels such as sodium, potassium, or calcium channels
- the excitatory amino acid systems e.g. blockade or modulation of NMDA receptors
- the inhibitory neurotransmitter systems e.g. enhancement of GABA release, or blockade of GABA-uptake or membrane stabilisation effects.

Current anti-convulsive medications include, but are not limited to, tiagabine, carbamazepine, sodium valproate, lamotrigine, gabapentin, pregabalin, ethosuximide, levetiracetam, phenytoin, topiramate, zonisamide as well as members of the benzodiazepine and barbiturate class.

An aspect of the invention provides a compound of formula I free base or a salt thereof for use as a medicament.

In one embodiment, the invention relates to the use of a compound of formula I free base or a salt thereof in a method of treatment.

An embodiment of the invention provides a pharmaceutical composition comprising a compound of formula I free base or a salt thereof and a pharmaceutically acceptable carrier or diluent. The composition may comprise any of the embodiments of formula I as described above.

A further embodiment of the invention relates to the use of a compound of formula I free base or a salt thereof for the preparation of a pharmaceutical composition for the treatment of a disease or disorder wherein a KCNQ potassium channel opener such as a KCNQ2 potassium channel opener is beneficial. Typically, such disorder or disease is selected from the group consisting of seizure disorders, anxiety disorders, neuropathic pain and migraine pain disorders, neurodegenerative disorders, stroke, cocaine abuse, nicotine withdrawal, ethanol withdrawal and tinnitus.

A further embodiment of the invention relates to the use of a compound of formula I free base or a salt thereof for the preparation of a pharmaceutical composition for the treatment of seizure disorders.

Typically, the seizure disorders to be treated are selected from the group consisting of acute seizures, convulsions, status epilepticus and epilepsy such as epileptic syndromes and epileptic seizures.

A further embodiment of the invention relates to the use of a compound of formula I free base or a salt thereof for the preparation of a pharmaceutical composition for the treatment of anxiety disorders.

Typically, the anxiety disorders to be treated are selected from the group consisting of anxiety and disorders and diseases related to panic attack, agoraphobia, panic disorder with agoraphobia, panic disorder without agoraphobia, agoraphobia without history of panic disorder, specific phobia, social phobia and other specific phobias, obsessive-compulsive disorder, posttraumatic stress disorder, acute stress disorders, generalized anxiety disorder, anxiety disorder due to general medical condition, substance-induced anxiety disorder, separation anxiety disorder, adjustment disorders, performance anxiety, hypochondriacal disorders, anxiety disorder due to general medical condition and substance-induced anxiety disorder and anxiety disorder not otherwise specified.

A further embodiment of the invention relates to the use of a compound of formula I free base or a salt thereof for the preparation of a pharmaceutical composition for the treatment of neuropathic pain and migraine pain disorders.

Typically, the neuropathic pain and migraine pain disorders to be treated are selected from the group consisting of allodynia, hyperalgesic pain, phantom pain, neuropathic pain related to diabetic neuropathy, neuropathic pain related to trigeminal neuralgia and neuropathic pain related to migraine.

A further embodiment of the invention relates to the use of a compound of formula I free base or a salt thereof for the preparation of a pharmaceutical composition for the treatment of neurodegenerative disorders.

Typically the neurodegenerative disorders to be treated are selected from the group consisting of Alzheimer's disease, Huntington's chorea, multiple sclerosis, amyotrophic lateral sclerosis, Creutzfeld-Jakob disease, Parkinson's disease, encephalopathies induced by AIDS or infection by rubella viruses, herpes viruses, borrelia and unknown pathogens, trauma-induced neurodegenerations, neuronal hyperexcitation states such as in medicament withdrawal or intoxication and neurodegenerative diseases of the peripheral nervous system such as polyneuropathies and polyneuritides.

A further embodiment of the invention relates to the use of a compound of formula I free base or a salt thereof for the preparation of a pharmaceutical composition for the treatment of bipolar disorders.

A further embodiment of the invention relates to the use of a compound of formula I free base or a salt thereof for the preparation of a pharmaceutical composition for the treatment of sleep disorders; such as insomnia.

The term "treatment" as used herein in connection with a disease or disorders includes also prevention, inhibition and amelioration as the case may be.

The invention provides compounds showing effect in at least one of the following tests:

"Relative efflux through the KCNQ2 channel" Which is a measure of the potency of the compound at the target channel "Maximum electroshock" Which is a measure of seizures induced by non-specific CNS stimulation by electrical means "Pilocarpine induced seizures" Seizures induced by pilocarpine are often difficult to treat with many existing antiseizure medications and so reflect a model of "drug resistant seizures"

"Electrical seizure-threshold tests" and "Chemical seizure-threshold tests" These models measure the threshold at which seizures are initiated, thus being models that detect whether compounds could delay seizure initiation.

"Amygdala kindling" Which is used as a measure of disease progression, as in normal animals the seizures in this model get more severe as the animal receives further stimulations.

"Electrophysiological patch-clamp recordings in CHO cells" and "electrophysiological recordings of KCNQ2, KCNQ2/KCNQ3 or KCNQ5 channels in oocytes"

In these tests voltage-activated KCNQ2, KCNQ2/KCNQ3 or KCNQ5 currents are recorded.

Pharmaceutical Compositions

The present invention also relates to a pharmaceutical composition. The compounds of the invention as the free base or salts thereof may be administered alone or in combination with pharmaceutically acceptable carriers or diluents, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the disorder or disease to be treated and the active ingredient chosen.

The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

The compounds of this invention are generally utilized as the free base or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

Pharmaceutical compositions for oral administration may be solid or liquid. Solid dosage forms for oral administration include e.g. capsules, tablets, dragees, pills, lozenges, powders, granules and tablette e.g. placed in a hard gelatine capsule in powder or pellet form or e.g. in the form of a troche or lozenge. Where appropriate, pharmaceutical compositions for oral administration may be prepared with coatings such as enteric coatings or they can be formulated so as to provide controlled release of the active ingredient such as sustained or prolonged release according to methods well known in the art. Liquid dosage forms for oral administration include e.g. solutions, emulsions, suspensions, syrups and elixirs.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid, lower alkyl ethers of cellulose, corn starch, potato starch, gums and the like. Examples of liquid carriers are syrup, peanut oil, olive oil, phospho lipids, fatty acids, fatty acid amines, polyoxyethylene and water.

The carrier or diluent may include any sustained release material known in the art, such as glyceryl monostearate or glyceryl distearate, alone or mixed with a wax.

Any adjuvants or additives usually used for such purposes such as colourings, flavourings, preservatives etc. may be used provided that they are compatible with the active ingredients.

The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants or diluents and subsequently compressing the mixture in a conventional tabletting machine.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferably from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the disorder or disease treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, such as about 0.01 to 100 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

Typical examples of recipes for the formulation of the invention are as follows:

1) Tablets containing 5.0 mg of a compound of the invention calculated as the free base:

| Compound of the invention | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| Compound of the invention | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per milliliter:

| Compound of the invention | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per milliliter:

| Compound of the invention | 0.5 mg |
| Sorbitol | 5.1 mg |
| Acetic Acid | 0.05 mg |
| Saccharin sodium | 0.5 mg |
| Water | ad 1 mL |

By the expression a compound of the invention is meant any one of the embodiments of formula I as described herein.

In a further aspect the present invention relates to a method of preparing a compound of the invention as described in the following.

Preparation of the Compounds of the Invention

The present invention relates to a compound represented by the general formula I:

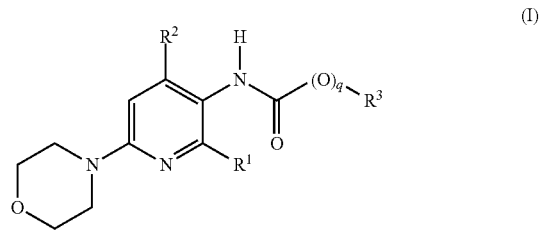

(I)

wherein q is 0 or 1;

each of $R^1$ and $R^2$ is independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-4}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy; and $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, optionally substituted Aryl-$C_{1-6}$-alk(en/yn)yl, optionally substituted Aryl-$C_{3-8}$-cycloalk(en)yl, optionally substituted Aryl-$C_{3-8}$-cycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, Heteroaryl-$C_{1-6}$-alk(en/yn)yl, Heteroaryl-$C_{3-8}$-cycloalk(en)yl, Heteroaryl-$C_{3-8}$-cycloalk(en)yl-$C_{1-6}$-alk(en/yn)yl, $NR^4R^5$—$C_{1-6}$-alk(en/yn)yl, $NR^4R^5$—$C_{3-8}$-cycloalk(en)yl, $NR^4R^5$—$C_{3-8}$-cycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-5}$-alk(en/yn)yl, halo-$C_{3-8}$-cycloalk(en)yl and halo-$C_{3-8}$-cycloalk(en)yl-$C_{1-6}$-alk(en/yn)yl; wherein each of $R^4$ and $R^5$ is independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

as the free base or salts thereof.

The compounds of the invention of the general formula I, wherein $R^1$, $R^2$, $R^3$ and q are as defined above may be prepared by the methods as represented in the schemes and as described below.

In the compounds of the general formulae I-XV, $R^1$, $R^2$, $R^3$ and q are as defined under formula I.

Compounds of the general formulae II, VII, VIII, IX, X, XI and XII are either obtained from commercial sources, or prepared by standard methods known to chemists skilled in the art.

Scheme 1.

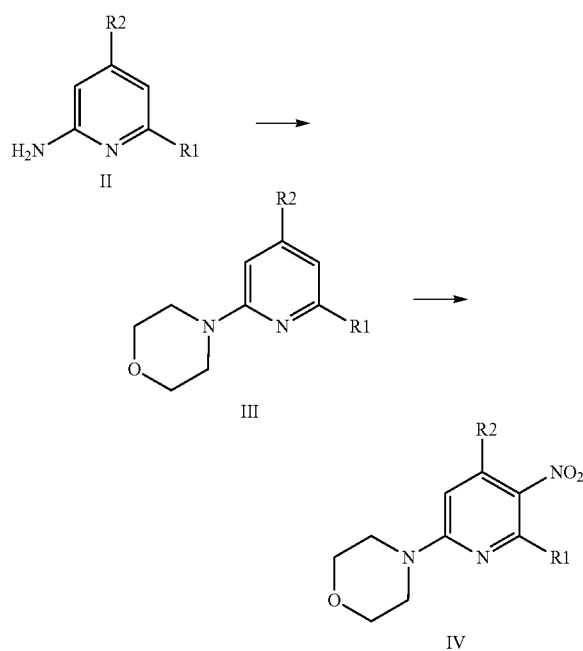

Compounds of the general formula III (scheme 1) may be prepared by reacting compounds of the general formula II with bis-(2-haloethyl)ethers, with or without the addition of bases, such as trialkyl amines, potassium carbonate or lithium-, sodium-, or potassium alcoholates, with or without the addition of catalysts such as sodium iodide, in a suitable solvent, such as dimethyl sulfoxide, N,N-dimethylformamide or ethanol, at a suitable temperature, such as room temperature or reflux temperature.

Compounds of the general formula IV (scheme 1) may be prepared from compounds of the general formula III, by nitration reactions known to chemists skilled in the art, such as reaction with concentrated nitric acid, sodium nitrite or sodium nitrate, in a suitable solvent, such as glacial acetic acid, acetic anhydride, trifluoroacetic acid, concentrated sulfuric acid or mixtures thereof, at appropriate temperatures, for example as described by P. B. D. de la Mare and J. H. Ridd, "Preparative methods of nitration" in *Aromatic substitutions*, pp. 48-56, Butterworths Scientific Publications, London, 1959.

Scheme 2.

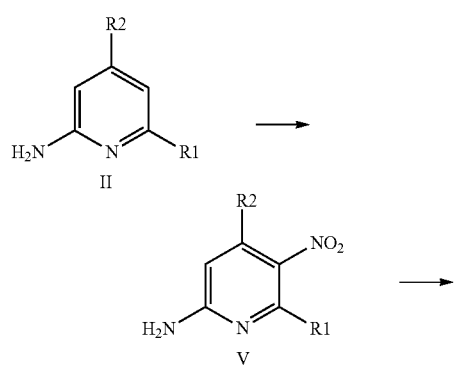

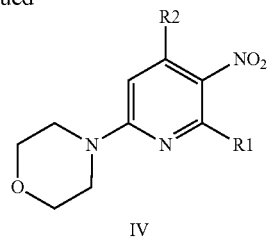

Compounds of the general formula V (scheme 2) may be prepared from compounds of the general formula II by nitration reactions known to chemists skilled in the art as described under scheme 1 for the preparation of compounds of the general formula IV.

Compounds of the general formula IV (scheme 2) may be prepared by reacting compounds of the general formula V with suitably substituted bis-(2-haloethyl)ethers as described under scheme 1 for the preparation of compounds of the general formula III.

Scheme 3.

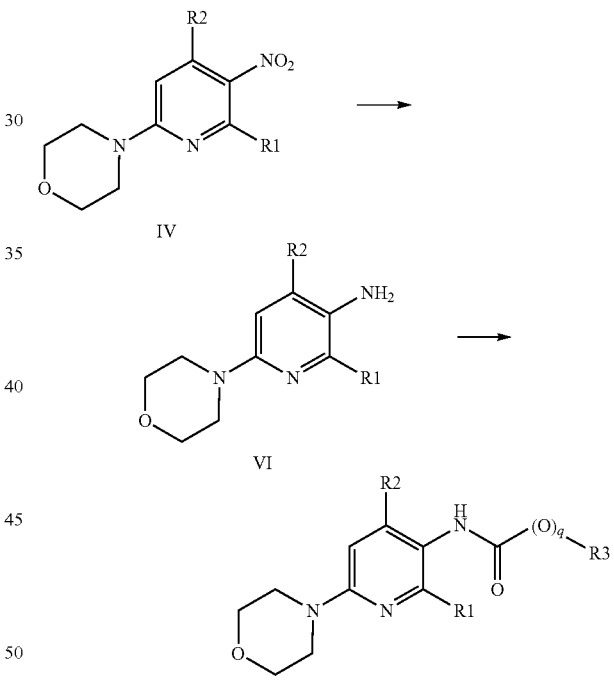

Compounds of the general formula VI (scheme 3) may be prepared from compounds of the general formula IV, by reducing the nitro group to an amino group, with suitable reducing agents such as zinc or iron powder in the presence of acid such as acetic acid or aqueous hydrochloric acid, or by hydrogen gas or ammonium formiate in the presence of a suitable hydrogenation catalyst such as palladium on activated carbon in suitable solvents such as methanol, ethanol, ethyl acetate or tetrahydrofuran, at suitable temperatures or under ultrasonic irradiation. Alternatively, tin (II) chloride or sodium dithionite can be used as reducing agents under conditions well known to chemists skilled in the art.

Compounds of the general formula I (scheme 3) may be prepared by reacting compounds of the general formula VI with suitable electrophilic reagents, such as, but not limited to, suitably substituted carboxylic acid fluorides, carboxylic acid chlorides, carboxylic acid bromides, carboxylic acid iodides, carboxylic acid anhydrides, activated esters, chloro formates, and with or without the addition of bases, such as pyridine, trialkyl amines, potassium carbonate, magnesium oxide or lithium-, sodium-, or potassium alcoholates, in a suitable solvent, such as ethyl acetate, dioxane, tetrahydrofuran, acetonitrile or diethyl ether, at suitable temperatures, such as room temperature or reflux temperature. Activated esters and carboxylic acid anhydrides can be prepared from suitably substituted carboxylic acids under conditions known to chemists skilled in the art, for example as described by F. Albericio and L. A. Carpino, "Coupling reagents and activation" in *Methods in enzymology: Solid-phase peptide synthesis*, pp. 104-126, Academic Press, New York, 1997. Carboxylic acid halides can be prepared from suitably substituted carboxylic acids by activation with reagents such as, but not limited to, thionyl chloride, oxalyl chloride, phosphorus tribromide or phosphorus triiodide under conditions well known to chemists skilled in the art.

Scheme 4.

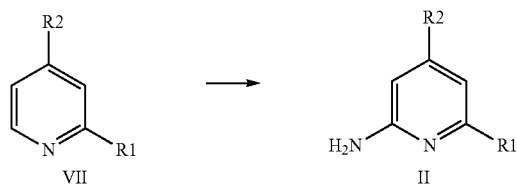

Compounds of the general formula II (scheme 4) may be prepared by reacting compounds of the general formula VII with sodium amide in a suitable solvent, such as xylene at a suitable temperature such as reflux temperature for example as described by J. Lecocq, *Bull. Soc. Chim. Fr.*, 1950, 188.

Scheme 5.

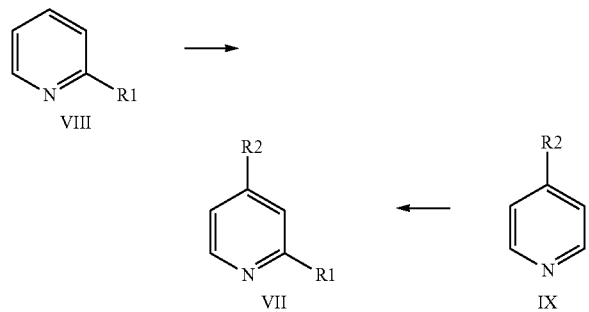

Compounds of the general formula VII, wherein $R^2$ is F, Cl, Br or I (scheme 5), may be prepared from compounds of the general formula VIII, by means of metallation and subsequent reaction with a suitable electrophile known to chemists skilled in the art, using appropriate bases such as butyllithium or lithium di-t-butyl(2,2,6,6-tetramethylpiperidino)zincate with subsequent addition of a suitable electrophile such as fluorine, chlorine, bromine, iodine, carbon tetrabromide or hexachloroethane in a suitable solvent such as heptane or tetrahydrofuran, at suitable temperatures, such as −78° C. or room temperature for example as described by F. Mongin and G. Quéguiner, *Tetrahedron*, 2001, 57, 4059.

Compounds of the general formula VII, wherein $R^1$ is F, Cl, Br or I (scheme 5), may be prepared from compounds of the general formula IX, by means of metallation and subsequent electrophilic aromatic substitution as described above.

Scheme 6.

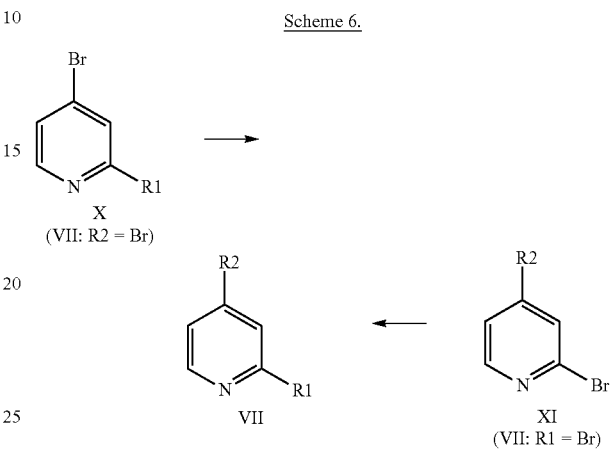

Compounds of the general formula VII, wherein $R^2$ is $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl or halo-$C_{3-8}$-cycloalk(en)yl-$C_{1-6}$-alk(en/yn)yl (scheme 6), may be prepared from compounds of the general formula X, by means of cross-coupling reactions known to chemists skilled in the art, such as Negishi coupling (E.-I. Negishi, A. O. King and N. Okukado, *J. Org. Chem.*, 1977, 42, 1821), Sonogashira coupling (K. Sonogashira, Y. Tohda and N. Hagihara, *Tet. Lett.*, 1975, 16, 4467), or other transition metal catalyzed cross-coupling reactions such as copper catalyzed reactions (W. Dohle, D. M. Lindsay and P. Knochel, *Org. Lett.*, 2001, 3, 2871).

Compounds of the general formula VII, wherein $R^1$ is $C_{1-6}$-alk(en/yn)yl, $C_{3-8}$-cycloalk(en)yl, $C_{3-8}$-cycloalk(en)yl-$C_{1-5}$-alk(en/yn)yl, halo-$C_{1-6}$-alk(en/yn)yl, halo-$C_{3-8}$-cycloalk(en)yl or halo-$C_{3-8}$-cycloalk(en)yl-$C_{1-6}$-alk(en/yn)yl (scheme 6), may be prepared from compounds of the general formula XI, by means of cross-coupling reactions as described above.

Additionally, compounds of the general formula VII, wherein $R^2$ is cyano (scheme 6), may be prepared from compounds of the general formula X, by means of nickel-catalyzed cyanation reactions known to chemists skilled in the art for example as described by L. Cassar, *Organomet. Chem.*, 1973, 54, C57-058.

Compounds of the general formula VII, wherein $R^1$ is cyano (scheme 6), may be prepared from compounds of the general formula XI, by means of nickel-catalyzed cyanation reactions as described above.

Compounds of the general formula VII, wherein $R^1=R^2$ (scheme 6), may be prepared from compounds of the general formula X, wherein $R^1=R^2=Br$, by means of cross-coupling reactions or cyanation reactions as described above.

Scheme 7.

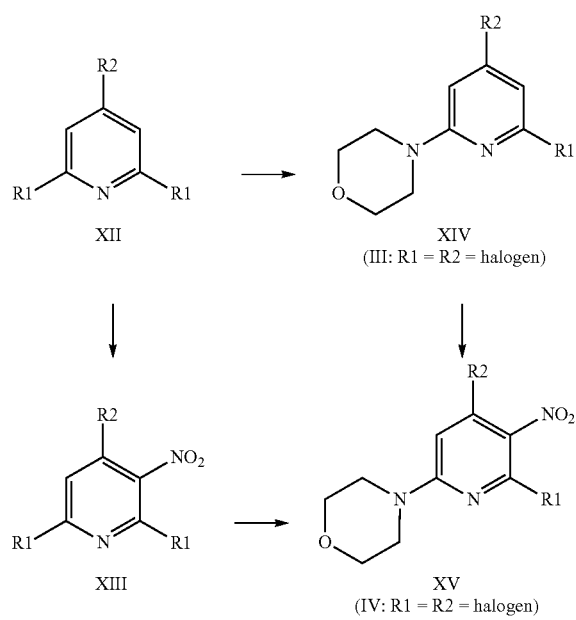

(III: R1 = R2 = halogen)

(IV: R1 = R2 = halogen)

Furthermore, compounds of general formula XIII (scheme 7), wherein R1 and R2 are halogen, can be prepared from 2,4,6-trihalopyridines of general formula XII, wherein R1 and R2 are halogen, by nitration reactions known to chemists skilled in the art as described under scheme 1 for the preparation of compounds of the general formula IV.

Compounds of general formula XIV (scheme 7), wherein R1 and R2 are halogen, may be prepared by from compounds of general type XII, wherein R1 and R2 are halogen, by reaction with morpholine in a suitable solvent such as dimethyl sulfoxide or N-methylpyrrolidinone, and with or without the addition of bases, such as pyridine, trialkyl amines, potassium carbonate, magnesium oxide, at suitable temperatures, such as room temperature or reflux temperature.

Compounds of general type XV may be prepared from compounds of general type XIII by reaction with morpholine in a suitable solvent such as dimethyl sulfoxide or N-methylpyrrolidinone, and with or without the addition of bases, such as pyridine, trialkyl amines, potassium carbonate, magnesium oxide, at suitable temperatures, such as room temperature or reflux temperature. Additionally, compounds of general type XV may be prepared from compounds of general type XIV by nitration reactions known to chemists skilled in the art as described under scheme 1 for the preparation of compounds of the general formula IV.

Furthermore, compounds of general formula IV, wherein $R^1$ or $R^2$ or both $R^1$ and $R^2$ is cyano (scheme 7), may be prepared from compounds of general formula XV, using cyanation reactions as described above. Compounds of general formula III, wherein $R^1$ or $R^2$ or both $R^1$ and $R^2$ is cyano, may be prepared from compounds of general formula XIV, using cyanation reactions as described above.

Compounds of the general formula III, wherein $R^1$ is $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl or halo-$C_{3-8}$-cycloalk(en)yl-$C_{1-6}$-alk(en/yn)yl (scheme 6), may be prepared from compounds of the general formula XIV, by means of cross-coupling reactions as described above (scheme 6).

Compounds of the general formula III, wherein $R^2$ is $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl or halo-$C_{3-8}$-cycloalk(en)yl-$C_{1-6}$-alk(en/yn)yl (scheme 6), may be prepared from compounds of the general formula XIV, by means of cross-coupling reactions as described above (scheme 6).

Compounds of the general formula IV, wherein $R^1$ is $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl or halo-$C_{3-8}$-cycloalk(en)yl-$C_{1-6}$-alk(en/yn)yl (scheme 6), may be prepared from compounds of the general formula XV, by means of cross-coupling reactions as described above (scheme 6), Compounds of the general formula IV, wherein $R^2$ is $C_{1-5}$-alk(en/yn)yl, $C_{3-8}$-cycloalk(en)yl, $C_{3-8}$-cyoloalk(en)yl-$C_{1-6}$-alk(en/yn)yl, halo-$C_{1-6}$-alk(en/yn)yl, halo-$C_{3-8}$-cycloalk(en)yl or halo-$C_{3-8}$-cycloalk(en)yl-$C_{1-5}$-alk(en/yn)yl (scheme 6), may be prepared from compounds of the general formula XV, by means of cross-coupling reactions as described above (scheme 6).

Compounds of general formula IV, wherein $R^1$ or $R^2$ or both $R^1$ and $R^2$ is $C_{1-6}$-alk(en/yn)yloxy, $C_{3-8}$-cycloalk(en)yloxy or $C_{3-8}$-cycloalk(en)yl-$C_{1-6}$-alk(en/yn)yloxy, may be prepared from compounds of general formula XV by reaction with the appropiate lithium-, sodium-, or potassium alcoholates or alcohols in the presence of base such as lithium-, sodium-, or potassium hydroxide, lithium-, sodium-, or potassium hydride, and with or without the addition of a catalyst such as copper sulfate, in a suitable solvent such as dioxane, at suitable temperatures, such as room temperature or reflux temperature.

Compounds of general formula III, wherein $R^1$ or $R^2$ or both $R^1$ and $R^2$ is $C_{1-6}$-alk(en/yn)yloxy, $C_{3-8}$-cycloalk(en)yloxy or $C_{3-8}$-cycloalk(en)yl-$C_{1-6}$-alk(en/yn)yloxy, may be prepared from compounds of general formula XIV by reaction with the appropiate lithium-, sodium-, or potassium alcoholates or alcohols in the presence of base such as lithium-, sodium-, or potassium hydroxide, lithium-, sodium-, or potassium hydride, and with or without the addition of a catalyst such as copper sulfate, in a suitable solvent such as dioxane, at suitable temperatures, such as room temperature or reflux temperature.

Additionally, for further variation of $R^1$ and $R^2$, compounds containing a methoxy-group, can be demethylated by methods known to chemists skilled in the art, such as treatment with boron tribromide in a suitable solvent, such as dichloromethane, at suitable temperatures, such as 0° C. or room temperature. The resulting phenols can then be alkylated by methods known to chemists skilled in the art. Such methods include: (a) the reaction with electrophiles, such as alkyl chlorides, alkyl bromides, alkyl iodides, carbonic acid chlorides, carbonic acid bromides, or carbonic acid anhydrides in the presence of suitable bases, such as potassium carbonate, in a suitable solvent, such as tetrahydrofuran, N,N-dimethylformamide, or 1,2-dichloroethane, at suitable temperatures, such as room temperature or reflux temperature; (b) the reaction with alkyl alcohols under conditions known as the Mitsunobu reaction (O. Mitsunobu, *Synthesis* 1981, 1).

Compounds containing functional groups, such as hydroxy groups, not compatible with suggested reaction conditions, can be protected and deprotected by methods known to chemists skilled in the art, for example as described by T. W. Greene and P. G. M. Wuts, *Protective groups in organic synthesis,* $2^{nd}$ edition, Wiley Interscience, 1991. In particular, hydroxy groups can be protected as, but not limited to, methyl-, tert-butyl-, trialkylsilyl-, triarylsilyl-, allyl- or trityl ethers.

Alkynes prepared by Sonogashira reactions may be reduced to alkenes or alkanes by reduction with hydrogen gas or ammonium formiate in the presence of a suitable hydrogenation catalyst such as palladium on activated carbon or platinum on activated carbon in suitable solvents such as methanol, ethanol or tetrahydrofuran, at suitable temperatures for example as described by S. Siegel, "Heterogeneous catalytic hydrogenation of C=C and alkynes" in *Comprehensive Organic Synthesis*, v. 8, pp. 417-442, Pergamon Press, 1991.

Preparation of the Compounds of the Invention

EXAMPLES

Analytical LC-MS data were obtained on a PE Sciex API 150EX instrument equipped with atmospheric pressure photo ionisation and a Shimadzu LC-8A/SLC-10A LC system.

Column: 30×4.6 mm Waters Symmetry C18 column with 3.5 µm particle size;

Solvent system: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

Preparative LC-MS-purification was performed on the same instrument with atmospheric pressure chemical ionisation. Column: 50×20 mm YMC ODS-A with 5 µm particle size;

Method: Linear gradient elution with 80% A to 100% B in 7 minutes and with a flow rate of 22.7 mL/minute. Fraction collection was performed by split-flow MS detection.

Analytical LC-MS-TOF (TOF=time of flight) data were obtained on a micromass LCT 4-ways MUX equipped with a Waters 2488/Sedex 754 detector system. Column: 30×4.6 mm Waters Symmetry C18 column with 3.5 µm particle size; Solvent system: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

GC-MS data were obtained on a Varian CP 3800 gaschromatograph fitted with a Phenomenex column (Zebron ZB-5, length: 15 meters, internal diameter: 0.25 mm) coupled to a Varian Saturn 2000 iontrap mass spectrometer. Method: Duration 15 minutes, column flow 1.4 mL/minute (carrier gas was helium), oven gradient: 0-1 minute, 60° C.; 1-13 minutes, 60-300° C.; 13-15 minutes, 300° C.

$^1$H NMR spectra were recorded at 500.13 MHz on a Bruker Avance DRX500 instrument. Deuterated dimethyl sulfoxide (99.8% D) was used as solvent. Tetramethylsilane was used as internal reference standard. Chemical shift values are expressed in ppm-values relative to tetramethylsilane. The following abbreviations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and b=broad singlet.

Preparation of Intermediates

4-(4,6-Dimethyl-pyridin-2-yl)-morpholine

2-Amino-4,6-dimethylpyridine (50 g), bis(2-chloroethyl) ether (57.5 mL), sodium iodide (6.13 g) and triethylamine (137 mL) were mixed in dry N,N-dimethylformamide (1 L) under argon and heated to 150° C. for 16 hours. Water/brine/saturated aqueous sodium bicarbonate (2:1:1, 750 mL) were added to the cooled reaction mixture and it was extracted with ethyl acetate (5×200 mL). The combined organic phases were concentrated in vacuo to app. 500 mL. Water (500 mL) and concentrated aqueous hydrochloric acid (35 mL) were added, the phases separated and the aqueous phase washed with ethyl acetate (200 mL). The aqueous phase was made basic with the addition of concentrated aqueous sodium hydroxide (50 mL) and extracted with isopropyl acetate (5×200 mL). The organic phase was dried over magnesium sulfate and concentrated in vacuo to furnish 44.0 g (56% yield) of the title compound as a black oil. The crude product was used without further purification. GC-MS (m/z) 192 (M); $t_R$=5.60. $^1$H NMR (500 MHz, DMSO-$d_6$): 2.08 (s, 3H), 2.26 (s, 3H), 3.39 (m, 4H), 3.68 (m, 4H), 6.05 (s, 1H), 6.44 (s, 1H).

4-(4,6-Dimethyl-5-nitro-pyridin-2-yl)-morpholine

To 4-(4,6-dimethyl-pyridin-2-yl)-morpholine (9.4 g) dissolved in trifluoroacetic acid (250 mL) cooled to 0° C. was added sodium nitrite (3.54 g) over 15 minutes and the reaction mixture was then stirred 15 minutes at 0° C. The reaction mixture was concentrated in vacuo to app. 100 mL and the pH adjusted to 11 with concentrated aqueous sodium hydroxide (150 mL). Brine (200 mL) was added and the mixture was extracted with diethyl ether (4×150 mL), the organic phase was dried over magnesium sulfate and concentrated in vacuo. The crude product was subjected to flash chromatography (SiO$_2$, heptane/ethylacetate 4:1) to furnish 2.01 g (17% yield) of the title compound as a yellow solid. GC-MS (m/z) 237 (M$^+$); $t_R$=7.69. $^1$H NMR (500 MHz, DMSO-$d_6$): 2.28 (s, 3H), 2.39 (s, 3H), 3.60 (m, 4H), 3.67 (m, 4H), 6.72 (s, 1H).

2,4-Dimethyl-6-morpholin-4-yl-pyridin-3-ylamine

Glacial acetic acid (25 mL) was added slowly to a mixture of zinc dust (2.76 g) and 4-(4,6-dimethyl-5-nitro-pyridin-2-yl)-morpholine (2.01 g) in tetrahydrofuran (100 mL) cooled to 0° C. The reaction mixture was then stirred for 16 hours at 25° C., filtered through celite, made basic with 25% aqueous ammonia and extracted with tetrahydrofuran (3×75 mL). The combined organic phases were dried over magnesium sulfate and concentrated in vacuo to furnish 1.76 g (100%) of the title compound as a dark red solid. GC-MS (m/z) 207 (M$^+$); $t_R$=7.27. $^1$H NMR (500 MHz, DMSO-$d_6$): 2.07 (s, 3H), 2.20 (s, 3H), 3.16 (m, 4H), 3.67 (m, 4H), 4.10 (b, 2H), 6.38 (s, 1H).

4-(4,6-Dichloropyridin-2-yl)-morpholine

Morpholine (5.0 g) was added to a suspension of 2,4,6-trichloropyridine (10.0 g) and sodium carbonate (5.9 g) in acetonitrile (100 mL). The reaction mixture was then stirred at 70° C. for 16 hours, cooled to ambient temperature, filtered through celite and concentrated in vacuo. The crude product was subjected to flash chromatography (SiO$_2$, heptane/ethylacetate 4:1) to furnish 3.90 g (30% yield) of the title compound as an off-white solid. LC-MS (m/z) 323.8 (M$^+$); $t_R$=3.10, (UV, ELSD) 98.5%, 98.9%. $^1$H NMR (500 MHz, CDCl$_3$): 3.50 (m, 4H), 3.80 (m, 4H), 6.45 (s, 1H), 6.67 (s, 1H).

4-(4,6-Dichloro-5-nitropyridin-2-yl)-morpholine

To a solution of 4-(4,6-dichloropyridin-2-yl)-morpholine (3.90 g) in concentrated sulfuric acid (40 mL) was added potassium nitrate (1.80 g) over 10 minutes. The reaction mixture was stirred for 16 hours at ambient temperature and then poured in to chrushed ice (500 g). The reaction mixture was made alkaline with concentrated sodium hydroxide and extracted with ethyl acetate (2×100 mL). The combined organic phases were dried over magnesium sulfate and concentrated in vacuo. The crude product was subjected to flash chromatography (SiO$_2$, heptane/ethylacetate 3:1) to furnish 2.26 g (49% yield) of the title compound as a yellow solid. LC-MS (n/z) 278.0 (M$^+$); t$_R$=3.10, (UV, ELSD) 96.5%, 98.8%. $^1$H NMR (500 MHz, CDCl$_3$): 3.62 (m, 4H), 3.80 (m, 4H), 6.50 (s, 1H).

4-(4-Chloro-6-methoxy-5-nitropyridin-2-yl)-morpholine and 4-(6-Chloro-4-methoxy-5-nitropyridin-2-yl)-morpholine To a solution of 4-(4,6-dichloro-5-nitropyridin-2-yl)-morpholine (2.02 g) in methanol (15 ml) was added sodium methoxide (0.98 g) and the mixture was heated for 16 hours at 65° C. After cooling to ambient temperature the reaction mixture was concentrated in vacuo. The crude product was subjected to flash chromatography (SiO$_2$, heptane/ethylacetate 3:1) to furnish 0.89 g (45% yield) of 4-(4-chloro-6-methoxy-5-nitropyridin-2-yl)-morpholine (fast eluting band) and 0.38 g (19%) of 4-(6-chloro-4-methoxy-5-nitropyridin-2-yl)-morpholine (late eluting band), both as yellow solids.
4-(4-chloro-6-methoxy-5-nitropyridin-2-yl)-morpholine: LC-MS (m/z) 273 (M$^+$); t$_R$=2.77, (UV, ELSD) 95%, 97%. $^1$H NMR (500 MHz, CDCl$_3$): 3.60 (m, 4H), 3.80 (m, 4H), 3.96 (s, 1H), 6.17 (s, 1H).
4-(6-chloro-4-methoxy-5-nitropyridin-2-yl)-morpholine: LC-MS (in/z) 273 (M); t$_R$=2.39, (UV, ELSD) 93%, 95%. $^1$H NMR (500 MHz, CDCl$_3$): 3.57 (m, 4H), 3.80 (m, 4H), 3.95 (s, 3H), 5.95 (s, 1H).

4-Chloro-2-methoxy-6-morpholin-4-ylpyridin-3-ylamine

To a solution of 4-(4-chloro-6-methoxy-5-nitropyridin-2-yl)-morpholine (0.82 g) in concentrated hydrochloric acid (50 mL) was added a solution of stannous dichloride (3.38 g) in concentrated hydrochloric acid (80 mL). The reaction mixture was heated to 75° C. for 1 hour and then poured on to chrushed ice (400 g) and extracted with ethyl acetate (2×100 mL). The combined organic phases were dried over magnesium sulfate and concentrated in vacuo, to furnish 0.45 g (61% yield) of the title compound as an off-white solid. LC-MS (m/z) 244 (M$^+$); t$_R$=1.48, (UV, ELSD) 89%, 94%. $^1$H NMR (500 MHz, CDCl$_3$): 3.30 (m, 4H), 3.65 (br s, 2H), 3.85 (m, 4H), 3.97 (s, 3H), 6.20 (s, 1H).

2-Chloro-4-methoxy-6-morpholin-4-ylpyridin-3-ylamine

To a solution of 4-(6-chloro-4-methoxy-5-nitropyridin-2-yl)-morpholine (0.38 g) in concentrated hydrochloric acid (20 mL) was added a solution of stannous dichloride (1.57 g) in concentrated hydrochloric acid (60 mL). The reaction mixture was heated to 75° C. for 5 minutes and then poured on to chrushed ice (100 g) and extracted with ethyl acetate (2×20 mL). The combined organic phases were dried over magnesium sulfate and concentrated in vacuo, to furnish 0.28 g (83% yield) of the title compound as an off-white solid. $^1$H NMR (500 MHz, CDCl$_3$): 3.35 (m, 4H), 3.65 (br s, 2H), 3.80 (m, 4H), 3.90 (s, 3H), 6.10 (s, 1H).

Compounds of the Invention

Acid addition salts of the compounds of the invention may easily be formed by methods known to the person skilled in the art.

Example 1

1aa (2,4-Dimethyl-6-morpholin-4-yl-pyridin-3-yl)-carbamic acid benzyl ester Benzyl chloroformate (18 mg) was added to a solution of 0.085 M 2,4-dimethyl-6-morpholin-4-yl-pyridin-3-ylamine and 0.17 M N,N-diisopropyl-ethylamine in 1,2-dichloroethane (1 mL). The vial was shaken for 16 hours under argon and concentrated in vacuo. Aqueous sodium hydroxide (1 M, 1 mL) was added and the crude mixture was extracted with isopropyl acetate/tetrahydrofuran (4:1, 2×1 mL). The organic phase was washed with brine (1 mL), concentrated in vacuo and redissolved in 1-propanol/dimethyl sulfoxide (1:1, 0.4 mL) of which 0.2 mL was subjected to preparative LC-MS purification to furnish 4.5 mg (31% yield) of the title compound as an oil. LC-MS (m/z) 342 (MH$^+$); t$_R$=1.58, (UV, ELSD) 99%, 99%.

The following compounds were prepared analogously:

1ab (2,4-Dimethyl-6-morpholin-4-yl-pyridin-3-yl)-carbamic acid 2-chloro-benzyl ester Yield: 18%. LC-MS (m/z) 376 (MH$^+$); t$_R$=1.78, (UV, ELSD) 99%, 100%.

1ac 2-(4-Chloro-phenyl)-N-(2,4-dimethyl-6-morpholin-4-yl-pyridin-3-yl)-acetamide Yield: 4%. LC-MS (m/z) 360 (MH$^+$); t$_R$=1.59, (UV, ELSD) 96%, 100%.

1ad 2-Phenyl-cyclopropanecarboxylic acid(2,4-dimethyl-6-morpholin-4-yl-pyridin-3-yl)-amide Yield: 24%. LC-MS (m/z) 352 (MH$^+$); t$_R$=1.64, (UV, ELSD) 96%, 100%.

1ae N-(2,4-Dimethyl-6-morpholin-4-yl-pyridin-3-yl)-2-thiophen-2-yl-acetamide Yield: 16%. LC-MS (m/z) 332 (MH$^+$); t$_R$=1.20, (UV, ELSD) 93%, 99%.

1af 3-Cyclohexyl-N-(2,4-dimethyl-6-morpholin-4-yl-pyridin-3-yl)-propionamide Yield: 15%. LC-MS (m/z) 346 (MH$^+$); t$_R$=1.81, (UV, ELSD) 91%, 100%.

1ag (2,4-Dimethyl-6-morpholin-4-yl-pyridin-3-yl)-carbamic acid isobutyl ester Yield: 29%. LC-MS (m/z) 308 (MH$^+$); t$_R$=1.44, (UV, ELSD) 97%, 99%.

1ah 3-(3-Chloro-phenyl)-N-(2,4-dimethyl-6-morpholin-4-yl-pyridin-3-yl)-propionamide 3-(3-Chlorophenyl)propionic acid (20 mg) was stirred at 25° C. for 2 hours under argon in oxalyl chloride (2 M in dichloromethane, 1 mL). The solvent was removed in vacuo and a solution of 0.085 M 2,4-dimethyl-6-morpholin-4-yl-pyridin-3-ylamine and 0.17 M N,N-diisopropyl-ethylamine in 1,2-dichloroethane (1 mL) was added to the reaction mixture. The vial was shaken for 16 hours under argon and concentrated in vacuo. Aqueous sodium hydroxide (1 M, 1 mL) was added and the crude mixture was extracted with isopropyl acetate/tetrahydrofuran (4:1, 2×1 mL). The organic phase was washed with brine (1 mL), concentrated in vacuo and redissolved in 1-propanol/dimethyl sulfoxide (1:1, 0.4 mL) of which 0.2 mL was subjected to preparative LC-MS purification to furnish 2.3 mg (14% yield) of the title compound as an oil. LC-MS (m/z) 374 (MH$^+$); $t_R$=1.71, (UV, ELSD) 99%, 99%.

The following compounds were prepared analogously:

1ai N-(2,4-Dimethyl-6-morpholin-4-yl-pyridin-3-yl)-2-(3,5-dimethyl-phenyl)-acetamide Yield: 19%. LC-MS (m/z) 354 (MH$^+$); $t_R$=1.69, (UV, ELSD) 99%, 99%.

1aj N-(2,4-Dimethyl-6-morpholin-4-yl-pyridin-3-yl)-3-p-tolyl-propionamide

Yield: 20%. LC-MS (m/z) 354 (MH$^+$); $t_R$=1.64, (UV, ELSD) 99%, 100%.

1ak 2-(3-Chloro-phenyl)-N-(2,4-dimethyl-6-morpholin-4-yl-pyridin-3-yl)-acetamide Yield: 14%. LC-MS (m/z) 360 (MH$^+$); $t_R$=1.58, (UV, ELSD) 97%, 99%.

1al 2-(3,4-Dichloro-phenyl)-N-(2,4-dimethyl-6-morpholin-4-yl-pyridin-3-yl)-acetamide Yield: 9%. LC-MS (m/z) 395 (MH$^+$); $t_R$=1.84, (UV, ELSD) 97%, 99%.

1am N-(2,4-Dimethyl-6-morpholin-4-yl-pyridin-3-y0-2-thiophen-3-yl-acetamide

Yield: 18%. LC-MS (m/z) 332 (MH$^+$); $t_R$=1.18, (UV, ELSD) 97%, 99%.

1an N-(2, 4-Dimethyl-6-morpholin-4-yl-pyridin-3-y0-2-p-tolyl-acetamide

Yield: 16%. LC-MS (m/z) 340 (MH$^+$); $t_R$=1.50, (UV, ELSD) 96%, 99%.

1ao 2-(3-Bromo-phenyl)-N-(2,4-dimethyl-6-morpholin-4-yl-pyridin-3-yl)-acetamide

Yield: 12%. LC-MS (m/z) 405 (MH$^+$); $t_R$=1.63, (UV, ELSD) 96%, 99%.

1ap N-(2,4-Dimethyl-6-morpholin-4-yl-pyridin-3-yl)-2-(3-trifluoromethyl-phenyl)-acetamide Yield: 20%. LC-MS (m/z) 394 (MH$^+$); $t_R$=1.77, (UV, ELSD) 94%, 99%.

1aq N-(2,4-Dimethyl-6-morpholin-4-yl-pyridin-3-yl)-2-phenyl-acetamide

Yield: 11%. LC-MS (m/z) 326 (MH$^+$); $t_R$=1.29, (UV, ELSD) 93%, 99%.

1ar 3,5,5-Trimethyl-hexanoic acid (2,4-dimethyl-6-morpholin-4-yl-pyridin-3-yl)-amide Yield: 20%. LC-MS (m/z) 348 (MH$^+$); $t_R$=1.97, (UV, ELSD) 93%, 99%.

1as Octanoic acid(2,4-dimethyl-6-morpholin-4-yl-pyridin-3-yl)-amide

Yield: 44%. LC-MS (m/z) 334 (MH$^+$); $t_R$=1.92, (UV, ELSD) 92%, 99%.

1at N-(2,4-Dimethyl-6-morpholin-4-yl-pyridin-3-yl)-2-naphthalen-2-yl-acetamide

Yield: 4%. LC-MS (in/z) 376 (MH$^+$); $t_R$=1.73, (UV, ELSD) 92%, 99%.

1au Heptanoic acid (2,4-dimethyl-6-morpholin-4-yl-pyridin-3-yl)-amide

Yield: 24%. LC-MS (m/z) 320 (MH$^+$); $t_R$=1.56, (UV, ELSD) 90%, 99%.

1ay N-(2,4-Dimethyl-6-morpholin-4-yl-pyridin-3-yl)-2-(3,4-climethyl-phenyl)-acetamide Yield: 26%. LC-MS (m/z) 354 (MH$^+$); $t_R$=1.65, (UV, ELSD) 77%, 99%.

1aw 2-Cyclohex-1-enyl-N-(2,4-dimethyl-6-morpholin-4-yl-pyridin-3-yl)-acetamide

Yield: 13%. LC-MS (m/z) 330 (MH$^+$); $t_R$=1.50, (UV, ELSD) 72%, 99%.

1ax N-(2,4-Dimethyl-6-morpholin-4-yl-pyridin-3-yl)-2-(4-methoxy-3-methyl-phenyl)-acetamide Yield: 16%. LC-MS (m/z) 370 (MH$^+$); $t_R$=1.56, (UV, ELSD) 94%, 99%.

1ay N-(2,4-Dimethyl-6-morpholin-4-yl-pyridin-3-yl)-2-(4-methoxy-phenyl)-acetamide Yield: 19%. LC-MS (m/z) 356 (MH$^+$); $t_R$=1.35, (UV, ELSD) 96%, 99%.

1az N-(2,4-Dimethyl-6-morpholin-4-yl-pyridin-3-yl)-3-(4-methoxy-phenyl)-propionamide Yield: 15%. LC-MS (m/z) 370 (MH$^+$); $t_R$=1.48, (UV, ELSD) 76%, 99%.

1ba N-(2,4-Dimethyl-6-morpholin-4-yl-pyridin-3-yl)-2-m-tolyl-aectamide m-Tolylacetic acid (0.33 g), N,N-diisopropyl-ethylamine (0.90 mL) and N-[(dimethylamino)-1H-1,2,3-triazolo-[4,5-b]pyridin-1-yl-methylene]-N-methyl-methanaminium hexafluoro-phosphate N-oxide (1.00 g) were mixed in dry N,N-dimethylformamide (3 mL) and stirred under argon for 2 minutes. 2,4-Dimethyl-6-morpholin-4-yl-pyridin-3-ylamine (0.30 g) dissolved in dry N,N-dimethylformamide (2 mL) was added to the reaction mixture, which was stirred at 25° C. under argon for 16 hours. Ethyl acetate (20 mL) was added and the organic phase was washed with saturated aqueous ammonium chloride/water (1:1, 20 mL), water (20 mL), brine/water (1:1, 20 mL), dried over sodium sulfate, concentrated in vacuo and purified by flash chromatography ($SiO_2$, heptane/ethylacetate 3:1) to furnish 0.069 g (14% yield) of the title compound as a white solid. LC-MS (m/z) 340 ($MH^+$); $t_R$=1.42, (UV, ELSD) 96%, 100%. $^1$H NMR (500 MHz, DMSO-$d_6$): 2.00 (s, 3H), 2.11 (s, 3H), 2.29 (s, 3H), 3.37 (m, 4H), 3.56 (s, 2H), 3.67 (m, 4H), 6.52 (s, 1H), 7.06 (d, 1H), 7.15 (m, 2H), 7.21 (t, 1H), 9.30 (s, 1H).

The following compounds were prepared analogously:

1bb N-(2,4-Dimethyl-6-morpholin-4-yl-pyridin-3-yl)-2-(4-fluoro-phenyl)-acetamide Yield: 14%. LC-MS (m/z) 344 ($MH^+$); $t_R$=1.34, (UV, ELSD) 99%, 99%. $^1$H NMR (500 MHz, DMSO-$d_6$): 1.99 (s, 3H), 2.10 (s, 3H), 3.37 (m, 4H), 3.60 (s, 2H), 3.66 (m, 4H), 6.52 (s, 1H), 7.16 (dd, 2H), 7.38 (dd, 2H), 9.33 (s, 1H).

1bc N-(2,4-Dimethyl-6-morpholin-4-yl-pyridin-3-yl)-3,3-dimethyl-butyramide

Yield: 53%. LC-MS (m/z) 306 (MH); $t_R$=1.26, (UV, ELSD) 99%, 98%. $^1$H NMR (500 MHz, DMSO-$d_6$): 1.05 (s, 9H), 2.07 (s, 3H), 2.18 (s, 2H), 2.19 (s, 3H), 3.37 (m, 4H), 3.67 (m, 4H), 6.54 (s, 1H), 9.01 (s, 1H).

1bd N-(2,4-Dimethyl-6-morpholin-4-yl-pyridin-3-yl)-2-(3-fluoro-phenyl)-acetamide Yield: 15%. LC-MS (m/z) 344 ($MH^+$); $t_R$=1.54, (UV, ELSD) 100%, 100%. $^1$H NMR (500 MHz, DMSO-$d_6$): 2.00 (s, 3H), 2.11 (s, 3H), 3.37 (m, 4H), 3.64 (s, 2H), 3.66 (m, 4H), 6.52 (s, 1H), 7.08 (dt, 1H), 7.18 (m, 2H), 7.38 (m, 1H), 9.34 (s, 1H).

1be 2-Bicyclo[2.2.1]hept-2-yl-N-(2,4-dimethyl-6-morpholin-4-yl-pyridin-3-yl)-acetamide Yield: 62%. LC-MS (m/z) 344 ($MH^+$); $t_R$=1.58, (UV, ELSD) 99%, 99%. $^1$H NMR (500 MHz, DMSO-$d_6$): 1.14 (m, 4H), 1.42 (m, 4H), 1.90 (m, 1H), 2.01 (m, 1H), 2.04 (s, 3H), 2.10 (m, 1H), 2.16 (s, 3H), 2.21 (m, 2H), 3.37 (m, 411), 3.67 (m, 4H), 6.53 (s, 1H), 9.04 (s, 1H).

1bf 2-(3,4-Difluoro-phenyl)-N-(2,4-dimethyl-6-morpholin-4-yl-pyridin-3-yl)-acetamide Yield: 9%. LC-MS (m/z) 362 ($MH^+$); $t_R$=1.52, (UV, ELSD) 95%, 99%. $^1$H NMR (500 MHz, DMSO-$d_6$): 2.00 (s, 3H), 2.11 (s, 3H), 3.37 (m, 4H), 3.63 (s, 2H), 3.66 (m, 4H), 6.52 (s, 1H), 7.19 (m, 1H), 7.39 (m, 2H), 9.32 (s, 1H).

1bg 4-Methyl-pentanoic acid (2,4-dimethyl-6-morpholin-4-yl-pyridin-3-yl)-amide Yield: 34%. LC-MS (m/z) 306 ($MH^+$); $t_R$=1.33, (UV, ELSD) 100%, 99%. $^1$H NMR (500 MHz, DMSO-$d_6$): 0.91 (d, 6H), 1.49 (dt, 2H), 1.58 (m, 1H), 2.04 (s, 3H), 2.16 (s, 3H), 2.28 (t, 2H), 3.37 (m, 4H), 3.67 (m, 4H), 6.53 (s, 1H), 9.07 (s, 1H).

1bh 2-Cyclopent-2-enyl-N-(2,4-dimethyl-6-morpholin-4-yl-pyridin-3-yl)-acetamide Yield: 13%. LC-MS (m/z) 316 ($MH^+$); $t_R$=1.25, (UV, ELSD) 97%, 94%. $^1$H NMR (500 MHz, DMSO-$d_6$): 1.51 (m, 1H), 2.05 (m, 1H), 2.06 (s, 3H), 2.17 (s, 3H), 2.26 (m, 2H), 2.35 (m, 2H), 3.07 (m, 1H), 3.38 (m, 4H), 3.68 (m, 4H), 5.73 (m, 1H), 5.77 (m, 1H), 6.54 (s, 1H), 9.09 (s, 1H).

1bi 2-Cyclohexyl-N-(2,4-dimethyl-6-morpholin-4-yl-pyridin-3-yl)-acetamide

Yield: 12%. LC-MS (m/z) 332 ($MH^+$); $t_R$=1.50, (UV, ELSD) 99%, 95%. $^1$H NMR (500 MHz, DMSO-$d_6$): 0.98 (m, 2H), 1.20 (m, 3H), 1.71 (m, 6H), 2.05 (s, 3H), 2.15 (d, 2H), 2.16 (s, 3H), 3.37 (m, 4H), 3.67 (m, 4H), 6.53 (s, 1H), 9.05 (s, 1H).

1bj 5-Methyl-hexanoic acid(2,4-dimethyl-6-morpholin-4-yl-pyridin-3-yl)-amide Yield: 40%. LC-MS-TOF (m/z) 320 ($M^+$); $t_R$=1.51, (UV, ELSD) 97%, 100%. $^1$H NMR (500 MHz, DMSO-$d_6$): 0.87 (d, 6H), 1.21 (m, 2H), 1.60 (m, 3H), 2.05 (s, 3H), 2.16 (s, 3H), 2.25 (t, 2H), 3.37 (m, 4H), 3.67 (m, 4H), 6.53 (s, 1H), 9.05 (s, 1H).

1bk 2-Cyclopentyl-N-(2,4-dimethyl-6-morpholin-4-yl-pyridin-3-yl)-acetamide 2,4-Dimethyl-6-morpholin-4-yl-pyridin-3-ylamine (0.22 g) and cyclopentylacetyl chloride (0.19 mL) were dissolved in acetonitrile (5 mL) and heated to 150° C. for 10 minutes in a sealed microwave process vial. The reaction mixture was concentrated in vacuo and purified by flash chromatography ($SiO_2$, heptane/ethylacetate 3:1) to furnish 0.17 g (49% yield) of the title compound as a white solid. LC-MS (m/z) 318 (MH); $t_R$=1.40, (UV, ELSD) 97%, 99%. $^1$H NMR (500 MHz, DMSO-$d_6$): 1.21 (m, 2H), 1.52 (m, 2H), 1.61 (m, 2H), 1.77 (m, 2H), 2.05 (s, 3H), 2.17 (s, 3H), 2.24 (m, 1H), 2.26 (m, 2H), 3.37 (m, 4H), 3.67 (m, 4H), 6.53 (s, 1H), 9.05 (s, 1H).

The following compounds were prepared analogously except 1bl and 1bm which were recrystallized from ethyl acetate after flash chromatography:

1bl 3-Cyloperol-N-(2,4-dimethyl-6-morpholin-4-yl-pyridin-3-yl)-propionamide

Yield: 34%. LC-MS (m/z) 332 ($MH^+$); $t_R$=1.57, (UV, ELSD) 99%, 99%. $^1$H NMR (500 MHz, DMSO-$d_6$): 1.11 (m, 2H), 1.49 (m, 2H), 1.60 (m, 4H), 1.77 (m, 3H), 2.04 (s, 3H), 2.16 (s, 3H), 2.28 (t, 2H), 3.37 (m, 4H), 3.67 (m, 4H), 6.53 (s, 1H), 9.06 (s, 1H).

1bm Hexanoic acid(2,4-dimethyl-6-morpholin-4-yl-pyridin-3-yl)-amide

Yield: 51%. LC-MS (m/z) 306 ($MH^+$); $t_R$=1.39, (UV, ELSD) 99%, 99%. $^1$H NMR (500 MHz, DMSO-$d_6$): 0.88 (t, 3H), 1.31 (m, 4H), 1.60 (m, 2H), 2.05 (s, 3H), 2.16 (s, 3H), 2.27 (t, 2H), 3.37 (m, 4H), 3.67 (m, 4H), 6.53 (s, 1H), 9.03 (s, 1H).

1bn N-(4-Chloro-2-methoxy-6-morpholin-4-yl-pyridin-3-yl)-2-cyclopentylacetamide Yield: 53%. LC-MS (m/z) 354 ($MH^+$); $t_R$=2.68, (UV, ELSD) 98%, 99%. $^1$H NMR (500 MHz, $CDCl_3$): 1.25 (m, 2H), 1.50-1.65 (m, 4H), 1.90 (m, 2H), 2.45 (m, 3H), 3.45 (m, 4H), 3.77 (m, 4H), 3.90 (s, 3H), 6.20 (s, 1H), 6.50 (s, 1H).

1bo N-(2-Chloro-4-methoxy-6-morpholin-4-yl-pyridin-3-yl)-2-cyclopentylacetamide Yield: 69%. LC-MS (m/z) 354 (MH$^+$); $t_R$=2.39, (UV, ELSD) 99%, 99%. $^1$H NMR (500 MHz, CDCl$_3$): 1.25 (m, 2H), 1.50-1.70 (m, 4H), 1.90 (m, 2H), 2.35 (m, 3H), 3.50 (m, 4H), 3.80 (m, 4H), 3.85 (s, 3H), 6.00 (s, 1H), 6.45 (s, 1H).

1bp N-(2-Chloro-4-methoxy-6-morpholin-4-yl-pyridin-3-yl)-3,3-dimethylbutyramide Yield: 56%. LC-MS (m/z) 342 (MH$^+$); $t_R$=2.31, (UV, ELSD) 99%, 99%. $^1$H NMR (500 MHz, CDCl$_3$): 1.10 (s, 9H), 2.25 (s, 2H), 3,50 (m, 4H), 3.77 (m, 4H), 3.85 (s, 3H), 6.00 (s, 1H), 6.45 (s, 1H).

1bq N-(4-Chloro-2-methoxy-6-morpholin-4-yl-pyridin-3-yl)-3,3-dimethylbutyramide Yield: 68%. LC-MS (m/z) 342 (MH$^+$); $t_R$=1.39, (UV, ELSD) 99%, 99%. $^1$H NMR (500 MHz, DMSO-d$_6$): 1.10 (s, 9H), 2.15 (s, 2H), 3.45 (m, 4H), 3.70 (m, 4H), 3.80 (s, 3H), 6.45 (s, 1H), 8.95 (s, 1H).

1br N-(4-Chloro-2-methoxy-6-morpholin-4-yl-pyridin-3-yl)-propionamide

Yield: 71%. LC-MS (m/z) 300 (MH$^+$); $t_R$=0.97, (UV, ELSD) 98%, 98%. $^1$H NMR (500 MHz, DMSO-d$_6$): 1.05 (t, 3H), 2.25 (q, 2H), 3.45 (m, 4H), 3.70 (m, 4H), 3.80 (s, 3H), 6.45 (s, 1H), 9.00 (s, 1H).

TABLE 1

Reagents used for the preparation of compounds in Example 1.

| Name | Supplier | CAS no. | Cat. no. |
|---|---|---|---|
| 1-Cyclohexenylacetic acid | Alfa | 18294-87-6 | 19462 |
| 3,4-Difluorophenylacetic acid | ABCR | 658-93-5 | F02874E |
| 3-Bromophenylacetic acid | Aldrich | 1878-67-7 | 28,886-1 |
| 3-Chlorophenylacetic acid | Aldrich | 1878-65-5 | C6,335-9 |
| 3-(Trifluoromethyl)phenylacetic acid | Aldrich | 351-35-9 | 19,335-6 |
| 2-Amino-4,6-dimethylpyridine | Aldrich | 5407-87-4 | A5,180-7 |
| 2-Chlorobenzyl chloroformate | Aldrich | 39545-31-8 | 49,379-1 |
| 2-Cyclopentene-1-acetic acid | Aldrich | 13668-61-6 | C11,285-2 |
| 2-Naphthylacetic acid | Aldrich | 581-96-4 | 31,791-8 |
| 2-Phenylacetic acid | Aldrich | 103-82-2 | P1,662-1 |
| 2,4,6-trichloropyridine | Aldrich | 16063-69-7 | 63,353-4 |
| 3-(3-Chlorophenyl)propionic acid | ABCR | 21640-48-2 | TWC2925 |
| 3-(4-Methoxyphenyl)propionic acid | Aldrich | 1929-29-9 | M2,352-7 |
| 3-(4-Methylphenyl)propionic acid | Aldrich | 1505-50-6 | 11,826-5 |
| 3,4-Dichlorophenylacetic acid | Aldrich | 5807-30-7 | 28,000-3 |
| 3,4-Dimethylphenylacetic acid | Vitas-M | 17283-16-8 | TBB000367 |
| 3,5,5-Trimethylhexanoic acid | Acros | 3302-10-1 | 26944-0250 |
| 3,5-Dimethylphenylacetic acid | ABCR | 42288-46-0 | C-42288-46 |
| 3-Cyclohexylpropionyl chloride | Acros | 39098-75-4 | 35071-0250 |
| 3-Cyclopentylpropionyl chloride | Aldrich | 104-97-2 | 26,859-3 |
| 3-Fluorophenylacetic acid | Aldrich | 331-25-9 | 24,804-5 |
| 4-Chlorophenylacetyl chloride | Lancaster | 25026-34-0 | 6317 |
| 4-Fluorophenylacetic acid | Aldrich | 405-50-5 | F1,330-4 |
| 4-Methoxy-3-methylphenylacetic acid | Vitas-M | 4513-73-9 | TBB000371 |
| 4-Methoxyphenylacetic acid | Aldrich | 104-01-8 | M1,920-1 |
| 4-Methylpentanoic acid | Aldrich | 646-07-1 | 27,782-7 |
| 5-Methylhexanoic acid | Matrix | 628-46-6 | 3527 |
| Benzyl chloroformate | Aldrich | 501-53-1 | 11,993-8 |

TABLE 1-continued

Reagents used for the preparation of compounds in Example 1.

| Name | Supplier | CAS no. | Cat. no. |
|---|---|---|---|
| Bicyclo[2.2.1]hept-2-yl-acetic acid | Aldrich | 1007-01-8 | 12,726-4 |
| Bis-(2-chloroethyl)ether | Aldrich | 111-44-4 | C4,113-4 |
| Cyclohexyl-acetic acid | Aldrich | 5292-21-7 | C10,450-7 |
| Cyclopentylacetyl chloride | Lancaster | 1122-99-2 | 14562 |
| Heptanoic acid | Aldrich | 111-14-8 | 14,687-0 |
| Hexanoyl chloride | Aldrich | 142-61-0 | 29,465-9 |
| Isobutyl chloroformate | Aldrich | 543-27-1 | 17,798-9 |
| m-Tolylacetic acid | Aldrich | 621-36-3 | T3,809-1 |
| N-[(Dimethylamino)-1H-1,2,3-triazolo[4,5-b] pyridin-1-ylmethylene]-N-methylmethanaminium hexafluorophosphate N-oxide | Fluka | 148893-10-1 | 11373 |
| Octanoic acid | Aldrich | 124-07-2 | 15,375-3 |
| Oxalyl chloride | Aldrich | 79-37-8 | 32,042-0 |
| p-Tolylacetic acid | Aldrich | 622-47-9 | T3,810-5 |
| sodium iodide | Aldrich | 7681-82-5 | 32,245-8 |
| sodium nitrite | Aldrich | 7632-00-0 | 51,091-2 |
| Tert-butylacetic acid | Aldrich | 1070-83-3 | B8,840-3 |
| Thiophen-2-acetyl chloride | Aldrich | 39098-97-0 | 19,599-5 |
| Thiophene-3-acetic acid | Aldrich | 6964-21-2 | 22,063-9 |
| Trans-2-phenyl-1-cyclopropanecarbonyl chloride | Aldrich | 939-87-7 | 13,430-9 |
| Zinc | Aldrich | 52374-36-4 | 20,998-8 |

In vitro and In vivo Testing

The compounds of the invention have been tested and shown effect in at least one of the below models:

Relative Efflux Through the KCNQ2 Channel.

This exemplifies a KCNQ2 screening protocol for evaluating compounds of the present invention. The assay measures the relative efflux through the KCNQ2 channel, and was carried out according to a method described by Tang et al. (Tang, W. et. al., J. Biomol. Screen. 2001, 6, 325-331) for hERG potassium channels with the modifications described below.

An adequate number of CHO cells stably expressing voltage-gated KCNQ2 channels were plated at a density sufficient to yield a confluent mono-layer on the day before the experiment. The cells were loaded with 1 µCi/ml [$^{86}$Rb] over night. On the day of the experiment cells were washed with a HBSS-containing buffer (Hanks balanced salt solution provided from Invitrogen, cat #14025-050). Cells were pre-incubated with drug for 30 minutes and the $^{86}$Rb$^+$ efflux was stimulated by a submaximal concentration of 15 mM potassium chloride in the continued presence of drug for additional 30 minutes. After a suitable incubation period, the supernatant was removed and counted in a liquid scintillation counter (Tricarb). Cells were lysed with 2 mM sodium hydroxide and the amount of $^{86}$Rb$^+$ was counted. The relative efflux was calculated $((CPM_{super}/(CPM_{super}+CPM_{cell}))_{Cmpd}/(CPM_{super}/(CPM_{super}+CPM_{cell}))_{15\ mM\ KCl})*100-100$.

The compounds of the invention have an EC$_{50}$ of less than 20000 nM, in most cases less than 2000 nM and in many cases less than 200 nM. Accordingly, the compounds of the invention are considered to be useful in the treatment of diseases associated with the KCNQ family potassium channels.

Electrophysiological Patch-Clamp Recordings in CHO Cells

Voltage-activated KCNQ2 currents were recorded from mammalian CHO cells by use of conventional patch-clamp recordings techniques in the whole-cell patch-clamp configuration (Hamill O P et.al. *Pflügers Arch* 1981; 391: 85-100). CHO cells with stable expression of voltage-activated KCNQ2 channels were grown under normal cell culture conditions in CO$_2$ incubators and used for electrophysiological recordings 1-7 days after plating. KCNQ2 potassium channels were activated by voltage steps up to +80 mV in increments of 5-20 mV (or with a ramp protocol) from a membrane holding potential between −100 mV and −40 mV (Tatulian L et al. *J Neuroscience* 2001; 21 (15): 5535-5545). The electrophysiological effects induced by the compounds were evaluated on various parameters of the voltage-activated KCNQ2 current. Especially effects on the activation threshold for the current and on the maximum induced current were studied.

Some of the compounds of the invention have been tested in this test. A left-ward shift of the activation threshold or an increase in the maximum induced potassium current is expected to decrease the activity in neuronal networks and thus make the compounds useful in diseases with increased neuronal activity—like epilepsy.

Electrophysiological Recordings of KCNQ2, KCNQ2/KCNQ3 or KCNQ5 Channels in Oocytes Voltage-activated KCNQ2, KCNQ2/KCNQ3 or KCNQ5 currents were recorded from *Xenopus* oocytes injected with mRNA coding for KCNQ2, KCNQ2+KCNQ3 or KCNQ5 ion channels (Wang et al., *Science* 1998, 282, 1890-1893; Lerche et al., *J Biol Chem* 2000, 275, 22395-400). KCNQ2, KCNQ2/KCNQ3 or KCNQ5 potassium channels were activated by voltage steps from the membrane holding potential (between −100 mV and −40 mV) up to +40 mV in increments of 5-20 mV (or by a ramp protocol). The electrophysiological effects induced by the compounds were evaluated on various parameters of the voltage-activated KCNQ2, KCNQ2/KCNQ3 or KCNQ5 currents. Especially effects on the activation threshold for the current and on the maximum induced current were studied.

The hyperpolarizing effects of some of the compounds were also tested directly on the membrane potential during current clamp.

Maximum Electroshock

The test was conducted in groups of male mice using corneal electrodes and administering a square wave current of 26 mA for 0.4 seconds in order to induce a convulsion characterised by a tonic hind limb extension (Wlaz et al. *Epilepsy Research* 1998, 30, 219-229).

Pilocarpine Induced Seizures

Pilocarpine induced seizures are induced by intraperitoneal injection of pilocarpine 250 mg/kg to groups of male mice and observing for seizure activity resulting in loss of posture within a period of 30 minutes (Starr et al. *Pharmacology Biochemistry and Behavior* 1993, 45, 321-325).

Electrical Seizure-Threshold Test

A modification of the up-and-down method (Kimball et al. *Radiation Research* 1957, 1-12) was used to determine the median threshold to induce tonic hind-limb extension in response to corneal electroshock in groups of male mice. The first mouse of each group received an electroshock at 14 mA, (0.4 s, 50 Hz) and was observed for seizure activity. If a seizure was observed the current was reduced by 1 mA for the next mouse, however, if no seizure was observed then the current was increased by 1 mA. This procedure was repeated for all 15 mice in the treatment group.

Chemical Seizure-Threshold Test

The threshold dose of pentylenetetrazole required to induce a clonic convulsion was measured by timed infusion of pentylenetetrazole (5 mg/mL at 0.5 mL/minute) into a lateral tail vein of groups of male mice (Nutt et al. *J Pharmacy and Pharmacology* 1986, 38, 697-698).

Amygdala Kindling

Rats underwent surgery to implantation of tri-polar electrodes into the dorsolateral amygdala. After surgery the animals were allowed to recover before the groups of rats received either varying doses of test compound or the drug's vehicle. The animals were stimulated with their initial after discharge threshold +25 µA daily for 3-5 weeks and on each occasion seizure severity, seizure duration, and duration of electrical after discharge were noted. (Racine. *Electroencephalography and Clinical Neurophysiology* 1972, 32, 281-294).

Side Effects

Central nervous system side-effects were measured by measuring the time mice would remain on rotarod apparatus (Capacio et al. *Drug and Chemical Toxicology* 1992, 15, 177-201); or by measuring their locomotor activity by counting the number of infra-red beams crossed in a test cage (Watson et al. *Neuropharmacology* 1997, 36, 1369-1375).

Hypothermic actions on the animals core body temperature of the compound were measured by either rectal probe or implanted radiotelemetry transmitters capable of measuring temperature (Keeney et al. *Physiology and Behaviour* 2001, 74, 177-184).

Pharmacokinetics

The pharmacokinetic properties of the compounds were determined via: i.v. and p.o. dosing to Sprague Dawley rats, and, thereafter, drawing blood samples over 20 hours. Plasma concentrations were determined with LC/MS/MS.

The invention claimed is:

1. A method of ameliorating or inhibiting a disease selected from the group consisting of epilepsy, bipolar disorder, neuropathic pain and migraine pain comprising administering a compound of formula I:

wherein:

q is 0 or 1;

each of $R^1$ and $R^2$ is independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-Cycloalk(en)yl-$C_{1-6}$-alk(en/yn)yloxy; and $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, optionally substituted aryl-$C_{1-6}$-alk(en/yn)yl, optionally substituted aryl-$C_{3-8}$-cycloalk(en)yl, optionally substituted aryl-$C_{3-8}$-cycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, $C_{3-8}$-heterocycloalk(en)yl-$C_{1-6}$-alk(en/yn)yl, heteroaryl-$C_{1-6}$-alk(en/yn)yl, heteroaryl-$C_{3-8}$-cycloalk(en)yl, heteroaryl-$C_{3-8}$-cycloalk(en)yl-$C_{1-6}$-alk(en/yn)yl, $NR^4R^5$—$C_{1-6}$-alk(en/yn)yl, $NR^4R^5$—$C_{3-8}$-cycloalk(en)yl, $NR^4R^5$—$C_{3-8}$-cycloalk(en)yl-$C_{1-6}$-alk(en/yn)yl, $C_{1-6}$-alk(en/yn)yloxy -$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk (en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl, wherein:

each of $R^4$ and $R^5$ is independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

or a pharmaceutically acceptable salt thereof to a subject in need thereof.

2. The method according to claim 1 wherein q is 0.

3. The method according to claim 1 wherein q is 1.

4. The method according to claim 2 wherein each of $R^1$ and $R^2$ is independently selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yloxy and halogen.

5. The method according to claim 4 wherein both $R^1$ and $R^2$ are $C_{1-6}$-alk(en/yn)yl.

6. The method according to claim 4 wherein $R^1$ is $C_{1-6}$-alk(en/yn)yloxy and $R^2$ is halogen, or wherein $R^1$ is halogen and $R^2$ is $C_{1-6}$-alk(en/yn)yloxy.

7. The method according to claim 2 wherein $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk (en/yn)yl, optionally substituted aryl-$C_{1-6}$-alk(en/yn)yl, optionally substituted aryl-$C_{3-8}$-cycloalk (en)yl, optionally substituted aryl-$C_{3-8}$-cycloalk(en)yl-$C_{1-6}$-alk(en/yn)yl, heteroaryl-$C_{1-6}$-alk (en/yn)yl, heteroaryl-$C_{3-8}$-cycloalk(en)yl, and heteroaryl-$C_{3-8}$-cycloalk(en)yl-$C_{1-6}$-alk (en/yn)yl.

8. The method according to claim 7 wherein $R^3$ is selected from the group consisting of $C_{1-8}$-alk(en/yn)yl, $C_{3-8}$-cycloalk(en)yl-$C_{1-6}$-alk(en/yn)yl, optionally substituted aryl-$C_{1-6}$-alk(en/yn)yl, optionally substituted aryl-$C_{3-8}$-cycloalk(en)yl and heteroaryl-$C_{1-6}$-alk(en/yn)yl.

9. The method according to claim 2 wherein the optionally substituted aryl-$C_{1-6}$-alk(en/yn)yl, optionally substituted aryl-$C_{3-8}$-cycloalk(en)yl, and optionally substituted aryl-$C_{3-8}$-cycloalk(en)yl-$C_{1-6}$-alk(en/yn)yl may be substituted with one or more substituent independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk (en)yloxy and $C_{3-8}$-cycloalk(en)yl-$C_{1-6}$-alk(en/yn)yloxy.

10. The method according to claim 2 wherein the optionally substituted aryl-$C_{1-6}$-alk(en/yn)yl, optionally substituted aryl-$C_{3-8}$-ycloalk (en)yl, and optionally substituted aryl-$C_{3-8}$-cycloalk(en)yl-$C_{1-6}$-alk(en/yn)yl may be substituted with one or more substituent independently selected from the group consisting of halogen, $C_{1-6}$-alk(en/yn)yl, halo-C1-6-alk(en/yn)yl and $C_{1-6}$-alk(en/yn)yloxy.

11. A method of ameliorating or inhibiting a disease selected from the group consisting of epilepsy, bipolar disorder, neuropathic pain and migraine pain comprising administering a compound selected from the group consisting of:

(2,4-Dimethyl-6-morpholin-4-yl-pyridin-3-yl)-carbamic acid benzyl ester;

(2,4-Dimethyl-6-morpholin-4-yl-pyridin-3-yl)-carbamic acid 2-chloro-benzyl ester;

2-(4-Chloro-phenyl)-(2,4-dimethyl-6-morpholin-4-yl-pyridin-3-yl)-acetamide;

2-Phenyl-cyclopropanecarboxylic acid(2,4-dimethyl-6-morpholin-4-yl-pyridin-3-yl)-amide;

N-(2,4-Dimethyl-6-morpholin-4-yl-pyridin-3-yl)-2-thiophen-2-yl-acetamide;

3-Cyclohexyl-N-(2,4-dimethyl-6-morpholin-4-yl-pyridin-3-yl)-propionamide;

(2,4-Dimethyl-6-morpholin-4-yl-pyridin-3-yl)-carbamic acid isobutyl ester;

3-(3-Chloro-phenyl)-N-(2,4-dimethyl-6-morpholin-4-yl-pyridin-3-yl)-propionamide;

N-(2,4-Dimethyl-6-morpholin-4-yl-pyridin-3-yl)-2-(3,5-dimethyl-phenyl)-acetamide;

N-(2,4-Dimethyl-6-morpholin-4-yl-pyridin-3-yl)-3-p-tolyl-propionamide;

2-(3-Chloro-phenyl)-N-(2,4-dimethyl-6-morpholin-4-yl-pyridin-3-yl)-acetamide;

2-(3,4-Dichloro-phenyl)-N-(2,4-dimethyl-6-morpholin-4-yl-pyridin-3-yl)-acetamide;

N-(2,4-Dimethyl-6-morpholin-4-yl-pyridin-3-yl)-2-thiophen-3-yl-acetamide;

N-(2,4-Dimethyl-6-morpholin-4-yl-pyridin-3-yl)-2-p-tolyl-acetamide;

2-(3-Bromo-phenyl)-N-(2,4-dimethyl-6-morpholin-4-yl-pyridin-3-yl)-acetamide;

N-(2,4-Dimethyl-6-morpholin-4-yl-pyridin-3-yl)-2-(3-trifluoromethyl-phenyl)-acetamide;

N-(2,4-Dimethyl-6-morpholin-4-yl-pyridin-3-yl)-2-phenyl-acetamide;

3,5,5-Trimethyl-hexanoic acid(2,4-dimethyl-6-morpholin-4-yl-pyridin-3-yl)-amide;

Octanoic acid(2,4-dimethyl-6-morpholin-4-yl-pyridin-3-yl)-amide;

N-(2,4-Dimethyl-6-morpholin-4-yl-pyridin-3-yl)-2-naphthalen-2-yl-acetamide;

Heptanoic acid(2,4-dimethyl-6-morpholin-4-yl-pyridin-3-yl)-amide;

N-(2,4-Dimethyl-6-morpholin-4-yl-pyridin-3-yl)-2-(3,4-dimethyl-phenyl)-acetamide;

2-Cyclohex-1-enyl-N-(2,4-dimethyl-6-morpholin-4-yl-pyridin-3-yl)-acetamide;

N-(2,4-Dimethyl-6-morpholin-4-yl-pyridin-3-yl)-2-(4-methoxy-3-methyl-phenyl)-acetamide;

N-(2,4-Dimethyl-6-morpholin-4-yl-pyridin-3-yl)-2-(4-methoxy-phenyl)-acetamide;

N-(2,4-Dimethyl-6-morpholin-4-yl-pyridin-3-yl)-3-(4-methoxy-phenyl)-propionamide;

N-(2,4-Dimethyl-6-morpholin-4-yl-pyridin-3-yl)-2-m-tolyl-acetamide;

N-(2,4-Dimethyl-6-morpholin-4-yl-pyridin-3-yl)-2-(4-fluoro-phenyl)-acetamide;

N-(2,4-Dimethyl-6-morpholin-4-yl-pyridin-3-yl)-3,3-dimethyl-butyramide;

N-(2,4-Dimethyl-6-morpholin-4-yl-pyridin-3-yl)-2-(3-fluoro-phenyl)-acetamide;

2-Bicyclo[2.2.1]kept-2-yl-N-(2,4-dimethyl-6-morpholin-4-yl-pyridin-3-yl)-acetamide;

2-(3,4-Difluoro-phenyl)-N-(2,4-dimethyl-6-morpholin-4-yl-pyridin-3-yl)-acetamide;

4-Methyl-pentanoic acid(2,4-dimethyl-6-morpholin-4-yl-pyridin-3-yl)-amide;

2-(Cyclopent-2-enyl)-N-(2,4-dimethyl-6-morpholin-4-yl-pyridin-3-yl)-acetamide;

2-Cyclohexyl-N-(2,4-dimethyl-6-morpholin-4-yl-pyridin-3-yl)-acetamide;

5-Methyl-hexanoic acid(2,4-dimethyl-6-morpholin-4-yl-pyridin-3-yl)-amide;

2-Cyclopentyl-N-(2,4-dimethyl-6-morpholin-4-yl-pyridin-3-yl)-acetamide;

3-Cyclopentyl-N-(2,4-dimethyl-6-morpholin-4-yl-pyridin-3-yl)-propionamide;

Hexanoic acid(2,4-dimethyl-6-morpholin-4-yl-pyridin-3-yl)-amide;

N-(4-Chloro-2-methoxy-6-morpholin-4-yl-pyridin-3-yl)-2-cyclopentylacetamide;

N-(2-Chloro-4-methoxy-6-morpholin-4-yl-pyridin-3-yl)-2-cyclopentylacetamide;

N-(2-Chloro-4-methoxy-6-morpholin-4-yl-pyridin-3-yl)-3,3-dimethylbutyramide;

N-(4-Chloro-2-methoxy-6-morpholin-4-yl-pyridin-3-yl)-3,3-dimethylbutyramide; and N-(4-Chloro-2-methoxy-6-morpholin-4-yl-pyridin-3-yl)-propionamide;

or pharmaceutically acceptable salt thereof to a subject in need thereof.

12. The method according to claim 11, wherein the compound is selected from the group consisting of:

(2,4-Dimethyl-6-morpholin-4-yl-pyridin-3-yl)-carbamic acid benzyl ester;

(2,4-Dimethyl-6-morpholin-4-yl-pyridin-3-yl)-carbamic acid 2-chloro-benzyl ester;

2-(4-Chloro-phenyl)-(2,4-dimethyl-6-morpholin-4-yl-pyridin-3-yl)-acetamide;

2-Phenyl-cyclopropanecarboxylic acid(2,4-dimethyl-6-morpholin-4-yl-pyridin-3-yl)-amide;

N-(2,4-Dimethyl-6-morpholin-4-yl-pyridin-3-yl)-2-thiophen-2-yl-acetamide;

3-Cyclohexyl-N-(2,4-dimethyl-6-morpholin-4-yl-pyridin-3-yl)-propionamide;

(2,4-Dimethyl-6-morpholin-4-yl-pyridin-3-yl)-carbamic acid isobutyl ester;

3-(3-Chloro-phenyl)-N-(2,4-dimethyl-6-morpholin-4-yl-pyridin-3-yl)-propionamide;

N-(2,4-Dimethyl-6-morpholin-4-yl-pyridin-3-yl)-2-(3,5-dimethyl-phenyl)-acetamide;

N-(2,4-Dimethyl-6-morpholin-4-yl-pyridin-3-yl)-3-p-tolyl-propionamide;

2-(3-Chloro-phenyl)-N-(2,4-dimethyl-6-morpholin-4-yl-pyridin-3-yl)-acetamide;

2-(3,4-Dichloro-phenyl)-N-(2,4-dimethyl-6-morpholin-4-yl-pyridin-3-yl)-acetamide;

N-(2,4-Dimethyl-6-morpholin-4-yl-pyridin-3-yl)-2-thiophen-3-yl-acetamide;

N-(2,4-Dimethyl-6-morpholin-4-yl-pyridin-3-yl)-2-p-tolyl-acetamide; and 2-(3-Bromo-phenyl)-N-(2,4-dimethyl-6-morpholin-4-yl-pyridin-3-yl)-acetamide;

or pharmaceutically acceptable salt thereof.

13. The method according to claim 11, wherein the compound is selected from the group consisting of:

N-(2,4-Dimethyl-6-morpholin-4-yl-pyridin-3-yl)-2-(3-trifluoromethyl-phenyl)-acetamide;

N-(2,4-Dimethyl-6-morpholin-4-yl-pyridin-3-yl)-2-phenyl-acetamide;

3,5,5-Trimethyl-hexanoic acid(2,4-dimethyl-6-morpholin-4-yl-pyridin-3-yl)-amide;

Octanoic acid(2,4-dimethyl-6-morpholin-4-yl-pyridin-3-yl)-amide;

N-(2,4-Dimethyl-6-morpholin-4-yl-pyridin-3-yl)-2-naphthalen-2-yl-acetamide;

Heptanoic acid(2,4-dimethyl-6-morpholin-4-yl-pyridin-3-yl)-amide;

N-(2,4-Dimethyl-6-morpholin-4-yl-pyridin-3-yl)-2-(3,4-dimethyl-phenyl)-acetamide;

2-(Cyclohex-1-enyl)-N-(2,4-dimethyl-6-morpholin-4-yl-pyridin-3-yl)-acetamide;

N-(2,4-Dimethyl-6-morpholin-4-yl-pyridin-3-yl)-2-(4-methoxy-3-methyl-phenyl)-acetamide;

N-(2,4-Dimethyl-6-morpholin-4-yl-pyridin-3-yl)-2-(4-methoxy-phenyl)-acetamide;

N-(2,4-Dimethyl-6-morpholin-4-yl-pyridin-3-yl)-3-(4-methoxy-phenyl)-propionamide;

N-(2,4-Dimethyl-6-morpholin-4-yl-pyridin-3-yl)-2-m-tolyl-acetamide;

N-(2,4-Dimethyl-6-morpholin-4-yl-pyridin-3-yl)-2-(4-fluoro-phenyl)-acetamide;

N-(2,4-Dimethyl-6-morpholin-4-yl-pyridin-3-yl)-3,3-dimethyl-butyramide; and

N-(2,4-Dimethyl-6-morpholin-4-yl-pyridin-3-yl)-2-(3-fluoro-phenyl)-acetamide;

or pharmaceutically acceptable salt thereof.

14. The method according to claim 11, wherein the compound is selected from the group consisting of:

2-Bicyclo[2.2.1]kept-2-yl-N-(2,4-dimethyl-6-morpholin-4-yl-pyridin-3-yl)-acetamide;

2-(3,4-Difluoro-phenyl)-N-(2,4-dimethyl-6-morpholin-4-yl-pyridin-3-yl)-acetamide;

4-Methyl-pentanoic acid(2,4-dimethyl-6-morpholin-4-yl-pyridin-3-yl)-amide;

2-Cyclopent-2-enyl-N-(2,4-dimethyl-6-morpholin-4-yl-pyridin-3-yl)-acetamide;

2-Cyclohexyl-N-(2,4-dimethyl-6-morpholin-4-yl-pyridin-3-yl)-acetamide;

5-Methyl-hexanoic acid(2,4-dimethyl-6-morpholin-4-yl-pyridin-3-yl)-amide;

2-Cyclopentyl-N-(2,4-dimethyl-6-morpholin-4-yl-pyridin-3-yl)-acetamide;

3-Cyclopentyl-N-(2,4-dimethyl-6-morpholin-4-yl-pyridin-3-yl)-propionamide;

Hexanoic acid(2,4-dimethyl-6-morpholin-4-yl-pyridin-3-yl)-amide;

N-(4-Chloro-2-methoxy-6-morpholin-4-yl-pyridin-3-yl)-2-cyclopentylacetamide;

N-(2-Chloro-4-methoxy-6-morpholin-4-yl-pyridin-3-yl)-2-cyclopentylacetamide;

N-(2-Chloro-4-methoxy-6-morpholin-4-yl-pyridin-3-yl)-3,3-dimethylbutyramide;

N-(4-Chloro-2-methoxy-6-morpholin-4-yl-pyridin-3-yl)-3,3-dimethylbutyramide; and N-(4-Chloro-2-methoxy-6-morpholin-4-yl-pyridin-3-yl)-propionamide; or a pharmaceutically acceptable salt thereof.

15. The method according to claim 11, wherein the disease is epilepsy.

16. The method according to claim 11, wherein the disease is bipolar disorder.

17. The method according to claim 11, wherein the disease is neuropathic pain

18. The method according to claim 11, wherein the disease is migraine pain.

* * * * *